(12) United States Patent
Saxena et al.

(10) Patent No.: US 11,998,614 B2
(45) Date of Patent: Jun. 4, 2024

(54) COMPOSITIONS AND METHODS FOR INDUCING SCARRING BY PERI-TUMORAL CELLS

(71) Applicant: Duke University, Durham, NC (US)

(72) Inventors: Tarun Saxena, Durham, NC (US); Ravi Bellamkonda, Durham, NC (US); Nassir Mokarram-Dorri, Atlanta, GA (US)

(73) Assignee: DUKE UNIVERSITY, Durham, NC (US)

(*) Notice: Subject to any disclaimer, the term of this patent is extended or adjusted under 35 U.S.C. 154(b) by 0 days.

(21) Appl. No.: 16/696,960

(22) Filed: Nov. 26, 2019

(65) Prior Publication Data

US 2020/0171168 A1 Jun. 4, 2020

Related U.S. Application Data

(60) Provisional application No. 62/771,309, filed on Nov. 26, 2018.

(51) Int. Cl.
| | | |
|---|---|---|
| *A61K 47/69* | (2017.01) | |
| *A61K 47/65* | (2017.01) | |
| *B82Y 5/00* | (2011.01) | |
| *C07K 14/705* | (2006.01) | |

(52) U.S. Cl.
CPC .......... *A61K 47/6929* (2017.08); *A61K 47/65* (2017.08); *C07K 14/705* (2013.01); *B82Y 5/00* (2013.01)

(58) Field of Classification Search
None
See application file for complete search history.

(56) References Cited

U.S. PATENT DOCUMENTS

| | | |
|---|---|---|
| 9,486,520 B2 | 11/2016 | Borrebaeck et al. |
| 2010/0062968 A1 | 3/2010 | Pulendran et al. |
| 2010/0323021 A1* | 12/2010 | Hosta ............... A61K 38/15 977/773 |
| 2011/0104293 A1 | 5/2011 | Pulendran et al. |
| 2011/0206618 A1* | 8/2011 | Sato ............... A61K 49/0017 424/9.6 |
| 2012/0156135 A1 | 6/2012 | Farokhzad et al. |

FOREIGN PATENT DOCUMENTS

CN 107296815 A 10/2017

OTHER PUBLICATIONS

Kim et al., J. Am. Chem. Soc., 2007, 129: 7661-7665.*
Fouillet et al., Acad. Radiol., 1995, 2: 576-583.*
Zhang, Thesis, 2008.*
Nakagawa et al., Sci. Technol. Adv. Mater., 2016, 17: 387-397.*
Xiao et al., Nanotechnology, 2010, 21: 1-8.*
Pillemer et al., J. Biol. Chem., 1941, 137: 139-142.*
Sigma datasheet, 2021.*
Lusic, Chem. Rev., 2013, 113: 1641-1666.*
Amicon User Guide, 2022.*
Betzer et al., Nanomedicine, online Jun. 16, 2017.*
Luche, Proteomics, 2003, 3: 249-253.*
Huang, Int. J. Mol. Sci., 2014, 15: 10169-10184.*
Clark, W. H., Tumour progression and the nature of cancer. Br J Cancer 1991, 64 (4), 631-44.
Munson, J. M.; Fried, L.; Rowson, S. A.; Bonner, M. Y.; Karumbaiah, L.; Diaz, B.; Courtneidge, S. A.; Knaus, U. G.; Brat, D. J.; Arbiser, J. L.; Bellamkonda, R. V., Anti-invasive adjuvant therapy with imipramine blue enhances chemotherapeutic efficacy against glioma. Sci Transl Med 2012, 4 (127), 127ra36.
Lyon, J. G.; Mokarram, N.; Saxena, T.; Carroll, S. L.; Bellamkonda, R. V., Engineering challenges for brain tumor Immunotherapy. Adv Drug Deliv Rev 2017, 114, 19-32.
Quail, D. F.; Joyce, J. A., Microenvironmental regulation of tumor progression and metastasis. Nat Med 2013, 19 (11), 1423-37.
Quail, D. F.; Joyce, J. A., The Microenvironmental Landscape of Brain Tumors. Cancer Cell 2017, 31 (3), 326-341.
Hwang, S. Y.; Yoo, B. C.; Jung, J. W.; Oh, E. S.; Hwang, J. S.; Shin, J. A.; Kim, S. Y.; Cha, S. H.; Han, I. O., Induction of glioma apoptosis by microglia-secreted molecules: The role of nitric oxide and cathepsin B. Biochim Biophys Acta 2009, 1793 (11), 1656-68.
Kees, T.; Lohr, J.; Noack, J.; Mora, R.; Gdynia, G.; Todt, G.; Ernst, A.; Radlwimmer, B.; Falk, C. S.; Herold-Mende, C.; Regnier-Vigouroux, A., Microglia isolated from patients with glioma gain antitumor activities on poly (I:C) stimulation. Neuro Oncol 2012, 14 (1), 64-78.
Sarkar, S.; Doring, A.; Zemp, F. J.; Silva, C.; Lun, X.; Wang, X.; Kelly, J.; Hader, W.; Hamilton, M.; Mercier, P.; Dunn, J. F.; Kinniburgh, D.; van Rooijen, N.; Robbins, S.; Forsyth, P.; Cairncross, G.; Weiss, S.; Yong, V. W., Therapeutic activation of macrophages and microglia to suppress brain tumor-initiating cells. Ann Neurosci 2013, 20 (4), 154.
International Search Report and Written Opinion issued in PCT application No. PCT/US2019/063462, dated Mar. 20, 2020.
Wadajkar, Aniket S. et al., 'Tumor-targeted nanotherapeutics: overcoming treatment barriers for glioblastoma', Wiley Interdisciplinary Reviews: Nanomedicine and Nanobiotechnology, 2017, vol. 9, e1439, pp. 1-17.
Roy, Aniruddha et al., 'Modifying the tumor microenvironment using nanoparticle therapeutics', Wiley Interdisciplinary Reviews: Nanomedicine and Nanobiotechnology, 2016, vol. 8, pp. 891-908.
Shevtsov, Maxim A. et al., 'Tumor targeting using magnetic nanoparticle Hsp70 conjugate in a model of C6 glioma', Neuro-Oncology, 2014, vol. 16, No. 1, pp. 38-49.

(Continued)

*Primary Examiner* — Ileana Popa

(74) *Attorney, Agent, or Firm* — Talem IP Law, LLP

(57) ABSTRACT

Compositions are provided, the compositions comprising: (1) a nanoparticle; (2) optionally, a linker and/or masking agent; and (3) a ligand configured to activate peri-tumoral cells to induce scarring by the peri-tumoral cells. In some aspects, administration of the compositions to a subject may generate an environment capable of walling-off and containing invasive tumors.

10 Claims, 9 Drawing Sheets

(56) References Cited

OTHER PUBLICATIONS

Mendes, Maria et al., 'Targeted theranostic nanoparticles for brain tumor treatment', Pharmaceutics, Oct. 9, 2018, vol. 10, article No. 181, pp. 1-47.
Papastefanaki, Florentia et al., 'Intraspinal delivery of polyethylene glycol-coated gold nanoparticles promotes functional recovery after spinal cord injury', Molecular Therapy, 2015, vol. 23, No. 6, pp. 993-1002.
Saxena, Tarun et al., 'Engineering controlled peritumoral inflammation to constrain brain tumor growth', Advanced Healthcare Materials, Dec. 11, 2018 (Epub), vol. 8, article No. 1801076, pp. 1-14.
Beauchesne, P., Extra-neural metastases of malignant gliomas: myth or reality? Cancers (Basel) 2011, 3 (1), 461-77.
Lun, M.; Lok, E.; Gautam, S.; Wu, E.; Wong, E. T., The natural history of extracranial metastasis from glioblastoma multiforme. J Neurooncol 2011, 105 (2), 261-73.
Cuddapah, V. A.; Robel, S.; Watkins, S.; Sontheimer, H., A neurocentric perspective on glioma invasion. Nat Rev Neurosci 2014, 15 (7), 455-65.
Hamilton, J. D.; Rapp, M.; Schneiderhan, T. M.; Sabel, M.; Hayman, A.; Scherer, A.; Kröpil, P.; Budach, W.; Kretschmar, U.; Arne Gerber, P., Glioblastoma multiforme metastasis outside the CNS: three case reports and possible mechanisms of escape. Journal of Clinical Oncology 2014, 32 (22), e80-e84.
Zagzag, D.; Salnikow, K.; Chiriboga, L.; Yee, H.; Lan, L.; Ali, M. A.; Garcia, R.; Demaria, S.; Newcomb, E. W., Downregulation of major histocompatibility complex antigens in invading glioma cells: stealth invasion of the brain. Lab Invest 2005, 85 (3), 328-41.
Silver, D. J.; Siebzehnrubl, F. A.; Schildts, M. J.; Yachnis, A. T.; Smith, G. M.; Smith, A. A.; Scheffler, B.; Reynolds, B. A.; Silver, J.; Steindler, D. A., Chondroitin sulfate proteoglycans potently inhibit invasion and serve as a central organizer of the brain tumor microenvironment. J Neurosci 2013, 33 (39), 15603-17.
Gu, L.; Mooney, D. J., Biomaterials and emerging anticancer therapeutics: engineering the microenvironment. Nat Rev Cancer 2016, 16 (1), 56-66.
Silver, J.; Miller, J. H., Regeneration beyond the glial scar. Nat Rev Neurosci 2004, 5 (2), 146-56.
Sofroniew, M. V., Molecular dissection of reactive astrogliosis and glial scar formation. Trends Neurosci 2009, 32 (12), 638-47.
Silver, D. J.; Silver, J., Contributions of chondroitin sulfate proteoglycans to neurodevelopment, injury, and cancer. Cun Opin Neurobiol 2014, 27, 171-8.
Gilbert, R. J.; McKeon, R. J.; Darr, A.; Calabro, A.; Hascall, V. C.; Bellamkonda, R. V., CS-4,6 is differentially upregulated in glial scar and is a potent inhibitor of neurite extension. Mol Cell Neurosci 2005, 29 (4), 545-58.
Galtrey, C. M.; Fawcett, J. W., The role of chondroitin sulfate proteoglycans in regeneration and plasticity in the central nervous system. Brain Res Rev 2007, 54 (1), 1-18.
Varga, I.; Hutoczki, G.; Szemcsak, C. D.; Zahuczky, G.; Toth, J.; Adamecz, Z.; Kenyeres, A.; Bognar, L.; Hanzely, Z.; Klekner, A., Brevican, neurocan, tenascin-C and versican are mainly responsible for the invasiveness of low-grade astrocytoma. Pathol Oncol Res 2012, 18 (2), 413-20.
Viapiano, M. S.; Bi, W. L.; Piepmeier, J.; Hockfield, S.; Matthews, R. T., Novel tumor-specific isoforms of BEHAB/ brevican identified in human malignant gliomas. Cancer Res 2005, 65 (15), 6726-33.
Karumbaiah, L.; Anand, S.; Thazhath, R.; Zhong, Y.; McKeon, R. J.; Bellamkonda, R. V., Targeted downregulation of N-acetylgalactosamine 4-sulfate 6-O-sulfotransferase significantly mitigates chondroitin sulfate proteoglycan-mediated Inhibition. Glia 2011, 59 (6), 981-96.
Mueller, M. M.; Fusenig, N. E., Friends or foes—bipolar effects of the tumour stroma in cancer. Nat Rev Cancer 2004, 4 (11), 839-49.
Wade, A.; Robinson, A. E.; Engler, J. R.; Petritsch, C.; James, C. D.; Phillips, J. J., Proteoglycans and their roles in brain cancer. FEBS J 2013, 280 (10), 2399-417.

Belting, M., Glycosaminoglycans in cancer treatment. Thromb Res 2014, 133 Suppl 2, S95-101.
Tom, V. J.; Steinmetz, M. P.; Miller, J. H.; Doller, C. M.; Silver, J., Studies on the development and behavior of the dystrophic growth cone, the hallmark of regeneration failure, in an in vitro model of the glial scar and after spinal cord Injury. J Neurosci 2004, 24 (29), 6531-9.
Mathieu, D.; Lecomte, R.; Tsanaclis, A. M.; Larouche, A.; Fortin, D., Standardization and detailed characterization of the syngeneic Fischer/F98 glioma model. Can J Neurol Sci 2007, 34 (3), 296-306.
Fitch, M. T.; Doller, C.; Combs, C. K.; Landreth, G. E.; Silver, J., Cellular and molecular mechanisms of glial scarring and progressive cavitation: in vivo and in vitro analysis of inflammation-induced secondary injury after CNS trauma. J Neurosci 1999, 19 (19), 8182-98.
Matsumura, Y.; Maeda, H., A new concept for macromolecular therapeutics in cancer chemotherapy: mechanism of tumoritropic accumulation of proteins and the antitumor agent smancs. Cancer Res 1986, 46 (12 Pt 1), 6387-92.
Onder, T. T.; Gupta, P. B.; Mani, S. A.; Yang, J.; Lander, E. S.; Weinberg, R. A., Loss of E-cadherin promotes metastasis via multiple downstream transcriptional pathways. Cancer Res 2008, 68 (10), 3645-54.
Laland, P.; Dedichen, J.; Laland, S.; Oftebro, R.; Thorsdalen, N.; Voss, J., A Water-Soluble Polypeptide Prepared from Zymosan. Nature 1963, 199, 465-7.
Waldmannová E., Caisová V., Fáberová J., Sváčková P., Kovářová M., Sváčková D., Kumžáková Z., Jačková A., Vácová N., Nedbalová P., Horká M., Kopecký J., Ženka J., The use of Zymosan A and bacteria anchored to tumor cells for effective cancer immunotherapy: B16-F10 murine melanoma model. International immunopharmacology 2016, 39, 295-306.
Dillon, S.; Agrawal, S.; Banerjee, K.; Letterio, J.; Denning, T. L.; Oswald-Richter, K.; Kasprowicz, D. J.; Kellar, K.; Pare, J.; van Dyke, T.; Ziegler, S.; Unutmaz, D.; Pulendran, B., Yeast zymosan, a stimulus for TLR2 and dectin-1, induces regulatory antigen-presenting cells and immunological tolerance. J Clin Invest 2006, 116 (4), 916-28.
Oliveira-Nascimento, L.; Massari, P.; Wetzler, L. M., The Role of TLR2 in Infection and Immunity. Front Immunol 2012, 3, 79.
Barbalat, R.; Lau, L.; Locksley, R. M.; Barton, G. M., Toll-like receptor 2 on inflammatory monocytes induces type I interferon in response to viral but not bacterial ligands. Nat Immunol 2009, 10 (11), 1200-7.
Michelucci, A.; Heurtaux, T.; Grandbarbe, L.; Morga, E.; Heuschling, P., Characterization of the microglial phenotype under specific pro-inflammatory and anti-inflammatory conditions: Effects of oligomeric and fibrillar amyloid-beta. J Neuroimmunol 2009, 210 (1-2), 3-12.
Liddelow, S. A.; Guttenplan, K. A.; Clarke, L. E.; Bennett, F. C.; Bohlen, C. J.; Schirmer, L.; Bennett, M. L.; Munch, A. E.; Chung, W. S.; Peterson, T. C.; Wilton, D. K.; Frouin, A.; Napier, B. A.; Panicker, N.; Kumar, M.; Buckwalter, M. S.; Rowitch, D. H.; Dawson, V. L.; Dawson, T. M.; Stevens, B.; Barres, B. A., Neurotoxic reactive astrocytes are induced by activated microglia. Nature 2017, 541 (7638), 481-487.
Phulwani, N. K.; Esen, N.; Syed, M. M.; Kielian, T., TLR2 expression in astrocytes is induced by TNF-alpha- and NF-kappaB-dependent pathways. J Immunol 2008, 181 (6), 3841-9.
Blanco, E.; Shen, H.; Ferrari, M., Principles of nanoparticle design for overcoming biological barriers to drug delivery. Nat Biotechnol 2015, 33 (9), 941-51.
Wilhelm, S.; Tavares, A. J.; Dai, Q.; Ohta, S.; Audet, J.; Dvorak, H. F.; Chan, W. C., Analysis of nanoparticle delivery to tumours. Nature Reviews Materials 2016, 1, 16014.
Pyonteck, S. M.; Akkari, L.; Schuhmacher, A. J.; Bowman, R. L.; Sevenich, L.; Quail, D. F.; Olson, O. C.; Quick, M. L.; Huse, J. T.; Teijeiro, V.; Setty, M.; Leslie, C. S.; Oei, Y.; Pedraza, A.; Zhang, J.; Brennan, C. W.; Sutton, J. C.; Holland, E. C.; Daniel, D.; Joyce, J. A., CSF-1R inhibition alters macrophage polarization and blocks glioma progression. Nat Med 2013, 19 (10), 1264-72.

(56) References Cited

OTHER PUBLICATIONS

Perrault, S. D.; Walkey, C.; Jennings, T.; Fischer, H. C.; Chan, W. C., Mediating tumor targeting efficiency of nanoparticles through design. Nano Lett 2009, 9 (5), 1909-15.

Qian, X.; Peng, X. H.; Ansari, D. O.; Yin-Goen, Q.; Chen, G. Z.; Shin, D. M.; Yang, L.; Young, A. N.; Wang, M. D.; Nie, S., In vivo tumor targeting and spectroscopic detection with surface-enhanced Raman nanoparticle tags. Nat Biotechnol 2008, 26 (1), 83-90.

Yeh, Y. C.; Creran, B.; Rotello, V. M., Gold nanoparticles: preparation, properties, and applications in bionanotechnology. Nanoscale 2012, 4 (6), 1871-80.

Thobhani, S.; Attree, S.; Boyd, R.; Kumarswami, N.; Noble, J.; Szymanski, M.; Porter, R. A., Bioconjugation and characterisation of gold colloid-labelled proteins. J Immunol Methods 2010, 356 (1-2), 60-9.

Sarkar, S.; Doring, A.; Zemp, F. J.; Silva, C.; Lun, X.; Wang, X.; Kelly, J.; Hader, W.; Hamilton, M.; Mercier, P.; Dunn, J. F.; Kinniburgh, D.; van Rooijen, N.; Robbins, S.; Forsyth, P.; Cairncross, G.; Weiss, S.; Yong, V. W., Therapeutic activation of macrophages and microglia to suppress brain tumor-initiating cells. Nat Neurosci 2014, 17 (1), 46-55.

Mehta, N.; Lyon, J. G.; Patil, K.; Mokarram, N.; Kim, C.; Bellamkonda, R. V., Bacterial Carriers for Glioblastoma Therapy. Mol Ther Oncolytics 2017, 4, 1-17.

Chow, R. D.; Guzman, C. D.; Wang, G.; Schmidt, F.; Youngblood, M. W.; Ye, L.; Errami, Y.; Dong, M. B.; Martinez, M. A.; Zhang, S.; Renauer, P.; Bilguvar, K.; Gunel, M.; Sharp, P. A.; Zhang, F.; Platt, R. J.; Chen, S., AAV-mediated direct in vivo CRISPR screen identifies functional suppressors in glioblastoma. Nat Neurosci 2017, 20 (10), 1329-1341.

Liotta, L. A., Tumor invasion and metastases: role of the basement membrane. Warner-Lambert Parke-Davis Award ecture. The American journal of pathology 1984, 117 (3), 339.

Tlsty, T. D.; Coussens, L. M., Tumor stroma and regulation of cancer development. Annu Rev Pathol 2006, 1, 119-50.

Dong, Y. C., et al., "Effect of Gold Nanoparticle Size on Their Properties as Contrast Agents for Computed Tomography", Scientific Reports, 9, 14912, Oct. 17, 2019; https://doi.org/10.1038/s41598-019-50332-8.

Shang, L., et al., "Engineered nanoparticles interacting with cells: size matters", J Nanobiotechnol 12, 5, Feb. 3, 2014, https://doi.org/10.1186/1477-3155-12-5.

Singh, P., et al., "Gold Nanoparticles in Diagnostics and Therapeutics for Human Cancer", Int. J. Mol. Sci., 19(7): 1979, Jul. 6, 2018, 16 pgs.

M. Cilia et al., "A Comparison of Protein Extraction Methods Suitable for Gel-Based Proteomic Studies of Aphid Proteins", J Biomol Tech. 2009;20(4):201-215.

National Center for Biotechnology Information. "PubChem Compound Summary for CID 9898671, Kahalalide F" PubChem, Jan. 15, 2023, 20 pages.

Extended European Search Report issued in EPO Application No. 19890311.4, dated Mar. 1, 2023, 10 pages.

Piryazev, A. P. et al., "Effect of Gold Nanoparticles on Production of Reactive Oxygen Species by Human Peripheral Blood Leukocytes Stimulated with Opsonized Zymosan," Bulletin of Experimental Biology and Medicine, Nov. 24, 2013 (Byulleten Eksperimental'noi Biologii i Meditsiny, Jul. 2013), pp. 101-103, vol. 156, issue 1.

Sung, SJ et al., "Yeast Mannans inhibit binding and phagocytosis of zymosan by mouse peritoneal macrophages," The Journal of Cell Biology, Jan. 1983, pp. 160-166, vol. 96, issue 1.

\* cited by examiner

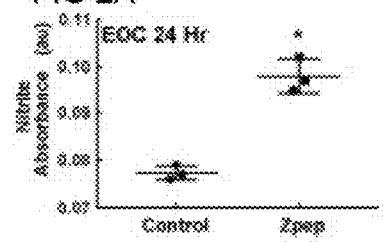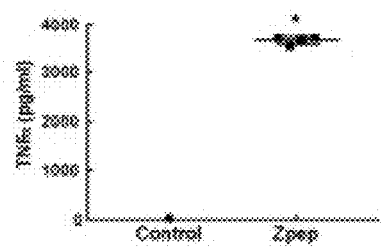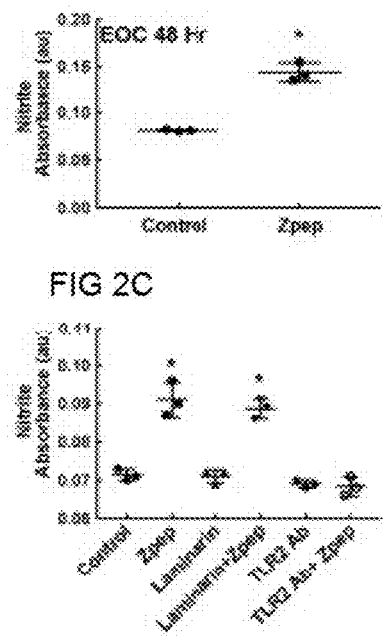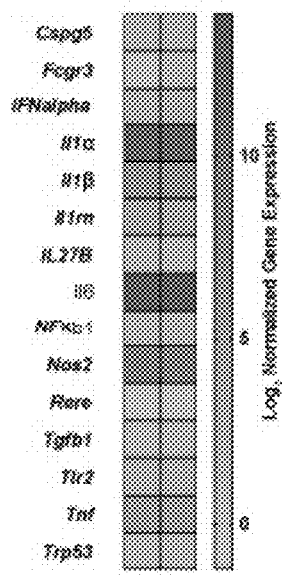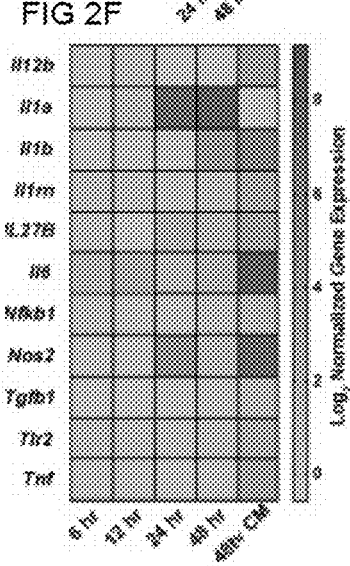
FIG 2

FIG 3A
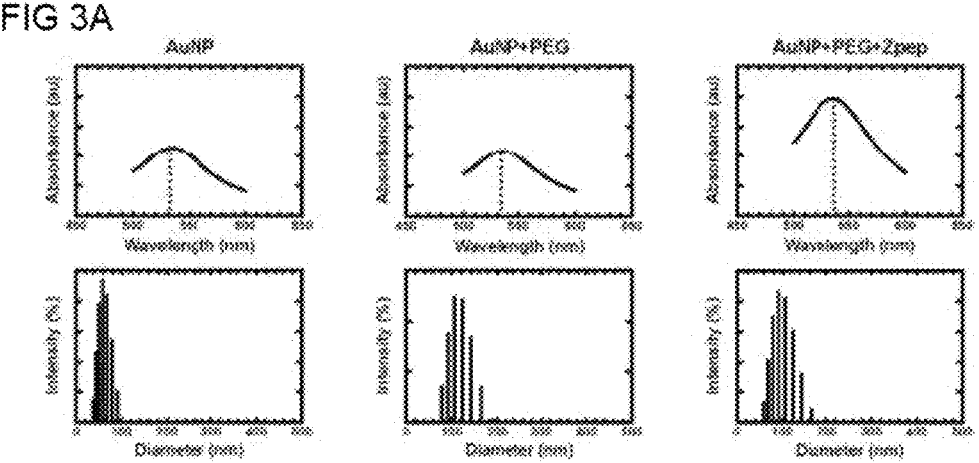
FIG 3B
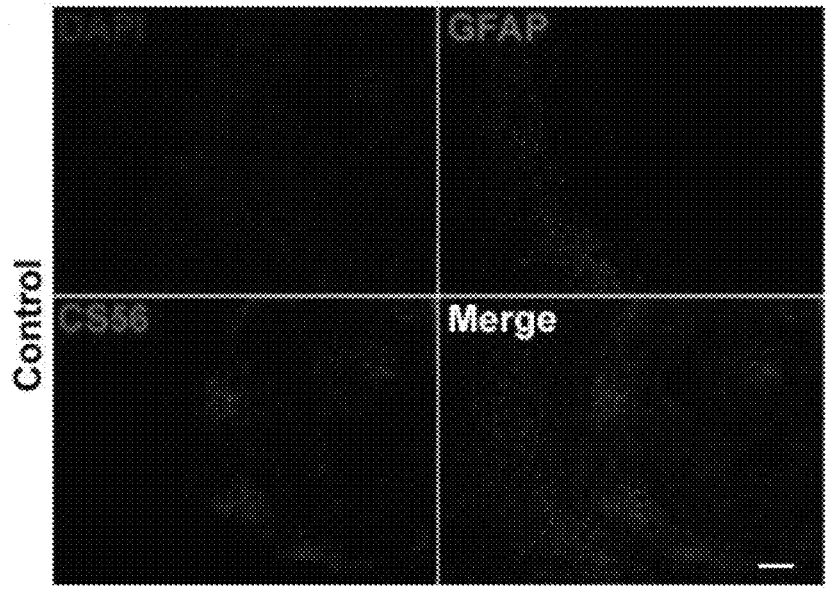
FIG 3C
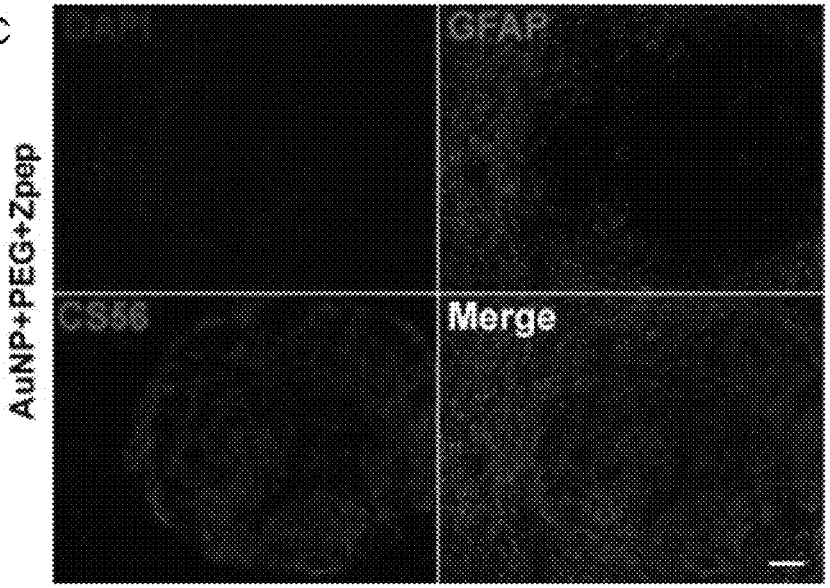
FIG 3

FIG 4A  AuNP+ PEG
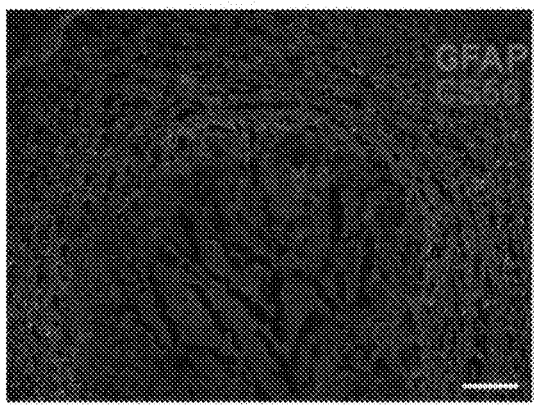
FIG 4B  Control　　　　　AuNP+ PEG　　　　AuNP+ PEG+Zpep
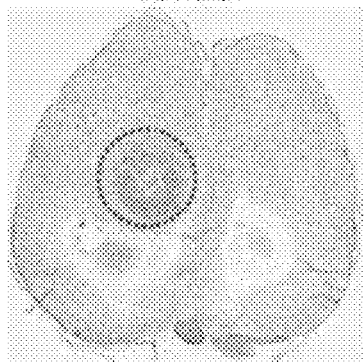 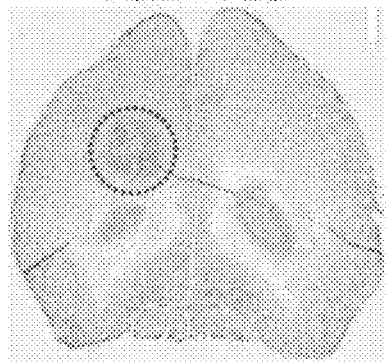 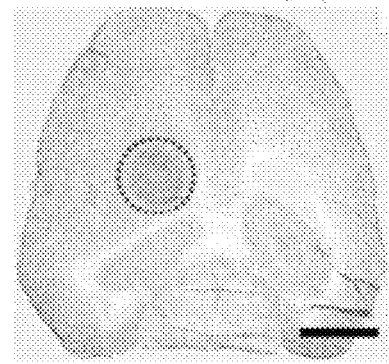
FIG 4

FIG 5A
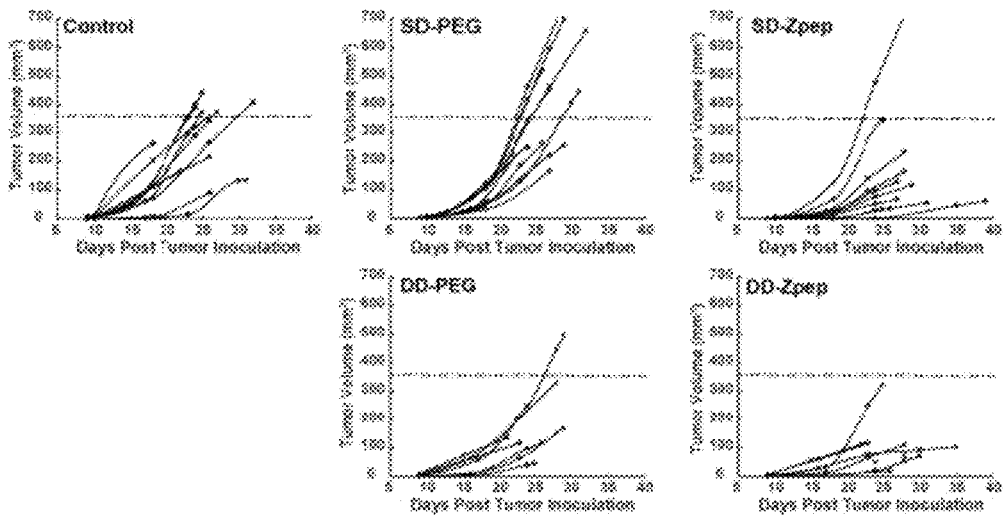
FIG 5B
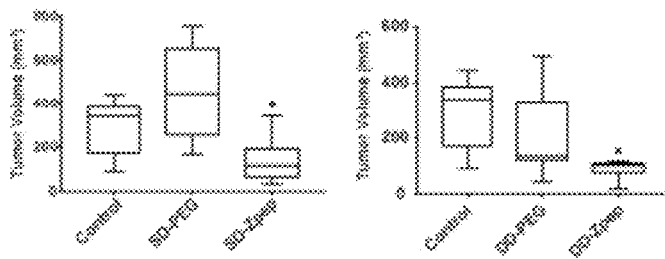
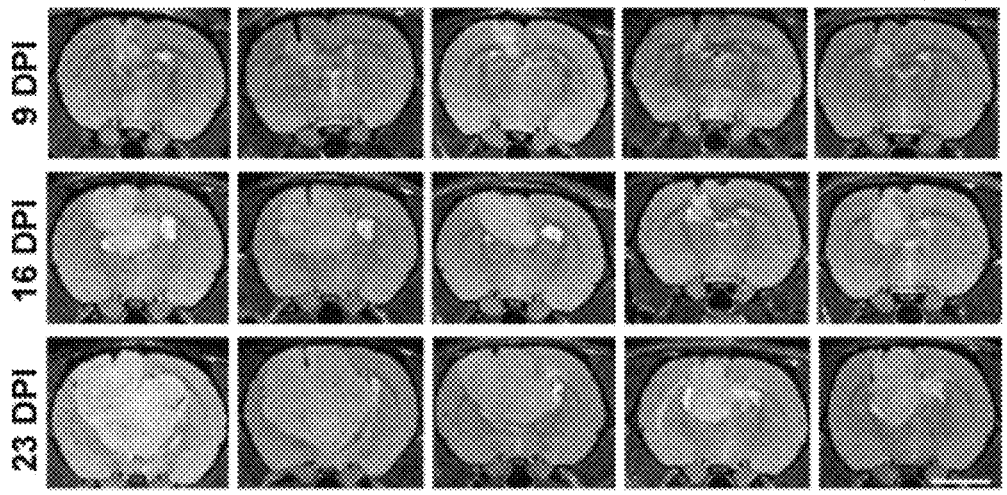
FIG 5

| NAME | Core Enrichment Genes |
|---|---|
| GO_LEUKOCYTE_MEDIATED_IMMUNITY | CADM1,CD74,C2,CTSC,ANXA3,MYO1G,CORO1A,C4A,C1QB,C3,C1QA,PRDX1,PTPN6,PI4K2A |
| GO_ADAPTIVE_IMMUNE_RESPONSE_BASED_ON_SOMATIC_RECOMBINATION_OF_IMMUNE_RECEPTORS_BUILT_FROM_IMMUNOGLOBULIN_SUPERFAMILY_DOMAINS | CADM1,CD74,C2,CTSC,MYO1G,C4A,C1QB,C3,C1QA |
| ONDER_CDH1_TARGETS_2_DN | SIRPA,CADM1,CTSC,ANXA3,CORO1A,C3,GPM6B,CNTN1,SNCA,NDRG1,CAMK2B,NRCAM,SLC1A3,SERPINA1,CA9,L1CAM,ARHGDIB |
| GO_LYMPHOCYTE_MEDIATED_IMMUNITY | CADM1,CD74,C2,CTSC,MYO1G,CORO1A,C4A,C1QB,C3,C1QA,PRDX1,PTPN6 |
| RAMALHO_STEMNESS_DN | SIRPA,CTSS,PTPRC,NCAM1,CORO1A,C3T3,CTSB,AP2A2,ITGB2,PACSIN1,BIN1,GRIA3 |
| GO_POSITIVE_REGULATION_OF_IMMUNE_RESPONSE | CADM1,HMGB2,CD74,C2,CTSS,PTPRC,GRB2,WAS,HLA-DRA,FCGR3A,MYO1G,PSMB10,THY1,C4A,C1QB,PSMA2,C3,C1QA,PSMB9,ARPC1B,PAK1,PTPRJ,PSMB8,ARPC4,ELMO1,ARPC3,PTPN6,CD180,PHB,ARPC2,UBE2K,CTSB,HRG,ITGB5 |
| GO_ADAPTIVE_IMMUNE_RESPONSE | CADM1,CD74,C2,CTSS,CTSC,MYO1G,TAP1,C4A,C1QB,C3,C1QA |
| GO_IMMUNE_EFFECTOR_PROCESS | CADM1,CD74,C2,PTPRC,GRB2,DHX58,WAS,CTSC,ANXA3,FCGR3A,MYO1G,CORO1A,ITGAL,B7AT2,C4A,C1QB,C3,C1QA,ARPC1B,PAK1,ARPC4,ELMO1,PRDX1,ARPC3,PTPN6,CD180,PI4K2A,ARPC2,LCP1,STAT1 |
| KEGG_FC_GAMMA_R_MEDIATED_PHAGOCYTOSIS | SCIN,DNM1L,PTPRC,WAS,FCGR3A,VASP,ARPC1B,PAK1,DNM1,ARPC4,ARPC3,ARPC2,MARCKS |
| GO_TRANSMEMBRANE_TRANSPORTER_ACTIVITY | ATP5I,COX8C,CYB5A,COX5A,TAPBP,SLC4A1,ATP6V0D1,VDAC1,ANXA5,SLC25A12,VDAC2,GPM6A,TAP1,ATP1B1,SLC25A5,SLC1A2,ATP6V0A1,ATP1A2,ATP8A1,SLC12A5,SLC2A4,SLC1A3,ATP6V1G2,SV2A,ATP2B2,ATP5J2,GRIA2,ATP1B2,ATP1A3,BSG,SLC8A2,ATP6V1B2,TTYH1,CALM1,ATP6V1A,ATP6A1,SLC25A11,DLG3,TF,UQCRB,CLIC1,ATP2B1,ATP6D,UQCRC1,SLC4A1,ATP2B4,ATP6V1E1,ATP1A1 |
| GO_REGULATION_OF_IMMUNE_EFFECTOR_PROCESS | CADM1,CD74,C2,PTPRC,DHX58,WAS,ANXA5,TAP1,STAT2,C4A,C3,ATP1B1,PPP3CB,SLC1A3,ELMO1,PTPN6,PHB,PHB2,AP2A2,ARP1,MIF,MDH1,LGALS3,RAC1,AP2B1,HPX,AP2M1,C1QBP,RAC2,C9,VAMP2 |
| GO_EXOCYTIC_VESICLE | SEPT8,DNM1L,ATP6V0D1,VDAC1,ANXA5,VDAC2,RAB3A,STX1B,SNCA,SYN1,DNM1,GAD2,SYNGR3,PI4K2A,SPTBN2,SV2A |
| LIU_VAV3_PROSTATE_CARCINOGENESIS_UP | CD74,CTSS,G6PZ,PSMB10,TAP1,C3,C1QA,PSMB9,PSMB8,ARHGDIB,ITGB2,STAT1,LGALS3 |
| MIKKELSEN_MEF_HCP_WITH_H3K27ME3 | CADM3,NTN1,CAMK2B,SLC12A5,SNCB,CRYM,SNAP25,SPTBN2,BCAN,PACSIN1,ATP2B2,GRIA2,ATP1A3,SLC8A2,BSN,TTYH1 |
| GO_REGULATION_OF_LYMPHOCYTE_MEDIATED_IMMUNITY | CADM1,PTPRC,WAS,TAP1,C3,PPP3CB,PTPN6 |
| GO_B_CELL_MEDIATED_IMMUNITY | CD74,C2,C4A,C1QB,C3,C1QA |
| GO_REGULATION_OF_IMMUNE_RESPONSE | CADM1,HMGB2,CD74,C2,CTSC,PTPRC,GRB2,DHX58,WAS,HLA-DRA,FCGR3A,MYO1G,PSMB10,ITGAL,TAP1,THY1,STAT2,C4A,C1QB,PSMA2,C3,C1QA,GPR1,PSMB9,ARPC1B,PAK1,PPP3CB,PTPRJ,PSMB8,ARPC4,CD81,ELMO1,ARPC3,PTPN6,CD180,PHB,ARPC2,UBE2K,AMBP,CTSB,PHB2,HRG,ITGB2,STAT1,UBE2N,MIF,LGALS3,RAC1,ICAM3,PSMD13,HPX,CALM1,C1QBP,RAC2,CD14,HRAS,HSP90B1,C9,VAMP2,KRT7 |
| GO_BLOOD_MICROPARTICLE | APOE,HBD,SLC4A1,ANXA5,HBB,HBA1,C44,C1QB,C3,CP,HP,AMBP,DNPEP,HRG,FGA,P2P,FGB,PFN1,AHSG,MSN,ITIH1,AGT,HPX,AFM,F2,C9,TF,KRT1,PLG,FGG,CLIC1 |
| GO_SUBSTANTIA_NIGRA_DEVELOPMENT | NDRG2,BASP1,INA,CKB,CNP,SIRT2,SYNGR3,G6PD,MAG,PLP1 |
| GO_TRANSPORT_VESICLE | SEPT8,YKT6,CD74,DNM1L,ARCN1,CTSC,ATP6V0D1,VDAC1,ANXA5,HLA-DRA,VDAC2,RAB3A,STX1B,CTSZ,SNCA,SYN1,DNM1,GAD2,SERPINA1,SYNGR3,PI4K2A,SPTBN2,CLTB,SV2A,SIPA1 |
| GO_HUMORAL_IMMUNE_RESPONSE | C3,PSMB10,C4A,C1QB,C3,C1QA,FGA,FGB,C1QBP,GPI,C9,KRT1 |
| GO_POSITIVE_REGULATION_OF_IMMUNE_SYSTEM_PROCESS | SCIN,CADM1,HMGB2,CD74,C2,CTSS,PTPRC,GRB2,DHX58,WAS,HLA-DRA,FCGR3A,MYO1G,PSMB10,CORO1A,TAP1,THY1,C4A,C1QB,PSMA2,C3,C1QA,PSMB9,ARPC1B,PAK1,PTPRJ,PSMB8,ARPC4,CD81,ELMO1,ARPC3,PTPN6,CD180,PHB,ARPC2,UBE2K,CTSB,AIF1,HRG,ITGB2,UBE2N,THBS1,MIF,PNP,LGALS3,RAC1,PSMD13,HPX,HCLS1,C1QBP,RAC2,CD14,HRAS,HSP90B1,C9,CALR,VAMP2,KRT1 |

FIG 7

| Ontology | Species | Name | DE Genes |
|---|---|---|---|
| GO:0019882 | RAT | Antigen processing and presentation | RT1-BA,PSMB8,CALR,CD74,CTSS,TAPBP,RT1-A2,WAS,RT1-BB,RT1-DA,RT1-DB1,LOC103689996 |
| GO:0002474 | RAT | Antigen processing and presentation (MHC clas | CALR,TAPBP,RT1-A2,LOC103689996 |
| GO:0002495 | RAT | Antigen processing and presentation (MHC clas | RT1-BA,CD74,RT1-BB,RT1-DA |
| KEGG:05330 | RAT | Allograft Rejection | RT1-BA,RT1-A2,RT1-CE7,RT1-BB,RT1-DA,RT1-DB1 |
| REAC:3000048 | HUMAN | Scavenging by Class A Receptors | APOE,HSP90B1,FTH1,CALR |
| GO:0061621 | HUMAN | Canonical Glycolysis | ENO1,PGK1,GPI,HK3 |
| REAC:70171 | HUMAN | Glycolysis | ENO1,PGK1,GPI,HK3 |
| GO:0050839 | HUMAN | Cell Adhesion Molecule Binding | ENO1,NDRG1,RARS,TMPO,IQGAP1,MSN,CADM3,CALR,CADM1,SPTAN1 |
| KEGG:04514 | RAT | Cell Adhesion Molecules | RT1-BA,PTPRC,CADM3,CADM1,RT1-A2,RT1-CE7,RT1-BB,RT1-DA,RT1-DB1 |

FIG 8

COMPOSITIONS AND METHODS FOR INDUCING SCARRING BY PERI-TUMORAL CELLS

RELATED U.S. APPLICATION DATA

This application claims priority to U.S. Provisional Patent Application No. 62/771,309, filed on Nov. 26, 2018, the entire contents of which are incorporated herein by reference.

BACKGROUND

Tumor treatment and metastasis prevention remain a challenge. This is particularly true where the tumors are difficult to access by conventional means. As an example, primary brain tumors are unique in that they rarely metastasize outside the brain. Nevertheless, brain tumors are characterized by high morbidity and mortality partly due to their localization and often locally invasive growth. Gliomas, tumors arising from glial cells, account for almost 30% of all primary brain tumors, and 80% of all malignant ones, and are responsible for the majority of deaths from primary brain tumors. WHO grade IV gliomas—glioblastoma multiforme (GBM)—are the most malignant and frequently occurring gliomas. For patients with newly diagnosed GBM, the therapeutic regimen is maximally-safe and feasible resection of the tumor mass, followed by concomitant and adjuvant temozolomide (TMZ) plus radiotherapy, followed by TMZ alone. Despite these measures, survival rates of GBM patients have remained dismal, with little improvement over the last 50 years. An important reason for this is that GBMs are highly invasive and can invade deep and into eloquent regions of the brain, making resections highly risky. Accordingly, there is a need for improved methods for treating brain tumors, and specifically for treating gliomas.

A critical determinant of brain tumor invasion is its extracellular matrix (ECM). In general, the ECM is a key component in the pathophysiology of nervous system injury. The ECM of the glial scar formed after traumatic brain or spinal cord injury is inhibitory to axonal regeneration. Glial scar ECM is rich in chondroitin sulfate proteoglycans (CSPGs), a diverse family of covalently linked protein-chondroitin sulfate (CS) glycosaminoglycan (GAG) polysaccharide complexes. The growth-promoting or inhibitory/repulsive effects of CSPGs are exerted predominantly by the various CS-GAGs that form the CSPGs. CSPG-rich glial scarring around sites of traumatic brain or spinal cord injury provides a critical barrier, quelling inflammation and preventing wider spread of tissue damage by "walling-off" the injury site.

With this in mind, what is needed are compositions and methods for targeting and activating peri-tumoral cells via a stimulus that recapitulates the sequelae of a traumatic CNS (central nervous system) injury, to generate an environment capable of walling-off and containing invasive tumors growth or spread by the inducement of scarring by the peritumoral cells.

SUMMARY

This Summary is provided to introduce a selection of concepts that are further described below in the Detailed Description. This Summary is not intended to identify key or essential features of the claimed subject matter; nor is this Summary intended to be used as an aid in limiting the scope of the claimed subject matter.

The present technology is directed to compositions and methods for inducing scarring of peri-tumoral cells to slow the growth of, contain, and/or substantially prevent the spread of cancerous cells from the treatment locus. Several aspects of the technology are directed to compositions and methods for inducing scarring of peri-tumoral cells by targeting and activating peri-tumoral cells with a stimulus that recapitulates the sequelae of a traumatic CNS injury. Such activation of the peri-tumoral cells creates a barrier or wall surrounding the existing tumor that is at least partically impermeable to tumor cells, thereby impeding invasive tumor growth or spread.

In one aspect, the present technology is directed to a composition compromising: (1) a nanoparticle; (2) optionally, a linker and/or a masking agent; and (3) a ligand configured to activate peri-tumoral cells to induce scarring by the peri-tumoral cells.

In one aspect, the present technology is directed to a composition comprising a conjugate, an encapsulate, or both. The conjugate, encapsulate, or both may compromise: (1) a nanoparticle; (2) optionally, a linker and/or a masking agent configured to enhance circulation time and prevent clearance of the nanoparticle from the bloodstream; and (3) a ligand, wherein the ligand is configured to target at least one of the following entities in a peri-tumoral cell: (i) toll-like receptor (TLR) 2; (ii) TLR4 receptor; (iii) CSF-1 receptor; (iv) IFN-gamma receptor 1; (v) IFN-gamma receptor 2; (vi) xylosyltransferase; (vii) tumor necrosis factor alpha (TNF-α) receptor; and (viii) IL-2 receptor. In some of the foregoing aspects, the linker and/or masking agent may comprise polyethylene glycol (PEG), a PEG derivative, or a hydrophilic polycarbonate. Additionally or alternatively, in some of the foregoing aspects the conjugate, encapsulate, or both have an average diameter of about 50 nm to about 200 nm.

In one aspect, a composition is provided, the composition comprising: (1) a nanoparticle; and (2) a ligand, wherein the ligand is configured to target at least one of the following entities in peri-tumoral cells: (i) a TLR2 receptor; (ii) a TLR4 receptor; (iii) a CSF-1 receptor; (iv) an IFN-gamma receptor 1; (v) an IFN-gamma receptor 2; (vi) xylosyltransferase; (vii) aTNF-alpha receptor; and/or (viii) an IL-2 receptor, and wherein the nanoparticle at least one of: (a) forms a conjugate with the ligand; and (b) encapsulates the ligand, and wherein the conjugate and/or encapsulate may have an average diameter sufficient to demonstrate an enhanced permeability and retention (EPR) effect and localize to peritumoral spaces when introduced intravenously. In one aspect, the composition further comprises PEG, a PEG derivative, a hydrophilic polycarbonate, or a derivative thereof.

According to some aspects of the technology, including any of the foregoing aspects, the nanoparticle may comprise a gold nanoparticle having an average diameter between about 5 nm-200 nm. In some aspects, the nanoparticle is a liposome having an average diameter between about 50 nm-200 nm.

According to some aspects of the technology, including any of the foregoing aspects, the ligand may comprise one or more of peptidoglycan, lipopolysaccharide (LPS), zymosan, Pam3CSK4, amyloid-beta peptide, lipoteichoic acid, high mobility group box 1 (HMGB1), heat shock proteins, CSF-1R inhibitors, LPS+IFN-gamma, xyloside, IFN-gamma, TNF-alpha, IL-2, lipocalin 2, and miRNA-155, a combination thereof, or a peptide or other mixture extracted or derived from any one or a combination of them. In one aspect, the ligand is a zymosan extract, referred to herein as ""Zpep.""

In one aspect, a composition comprising a conjugate is provided, the conjugate comprising: (1) a gold nanoparticle; (2) a linker and/or masking agent; and (3) Zpep.

In another aspect, methods are provided for the preparation of the conjugates and encapsulates provided herein.

According to some aspects of the present technology, a method is provided for activating peri-tumoral cells to induce scarring. In one aspect, this activation may be defined by a process such as the production of ECM molecules that are inhibitory to neural and glial migration, by the peri-tumoral cells. In one aspect, the method comprises administering a nanoparticle composition to target cells in close proximity to tumors in order to activate the cells and stimulate scarring. In one aspect, the method comprises administering gold nanoparticles coated with polypeptides to target stromal cells in close proximity to GBM tumors in order to activate the cells and stimulate stromal chondroitin sulfate proteoglycans (CSPG) expression.

Several aspects of the present technology include methods for slowing or substantially preventing tumor growth or spread of a tumor by inducing scarring of peri-tumoral tissue. In some aspects, inducing scarring includes administering a composition to a patient that targets cells in close proximity to tumors in order to activate the cells and stimulate scarring. In some aspects, the compositions include one or more nanoparticles and one or more ligands carried by the nanoparticles that are configured to activate peri-tumoral cells and induce scarring thereof.

BRIEF DESCRIPTION OF THE FIGURES

The description and claims may be more readily understood by reference to the following figures.

FIG. 2 ((a)-(f)) shows the effects of Zpep on glial cell activation.

FIG. 3 ((a)-(c)) shows the effects of using a conjugate comprising gold nanoparticles, PEG, and Zpep (the conjugate is referred to herein as ""AuNP—Z"") to stimulate peri-tumoral CSPG expression in vivo.

FIG. 4 ((a)-(b)) shows the effects of using AuNP—Z to constrain tumors in vivo.

FIG. 5 ((a)-(c)) shows the effects of using AuNP—Z to curtail tumor growth.

FIG. 7 shows the results of a gene set enrichment analysis of AuNP—Z-treated animals relative to controls.

FIG. 8 shows the results of an overrepresentation analysis of AuNP—Z-treated animals relative to controls.

DETAILED DESCRIPTION

Figure 1:
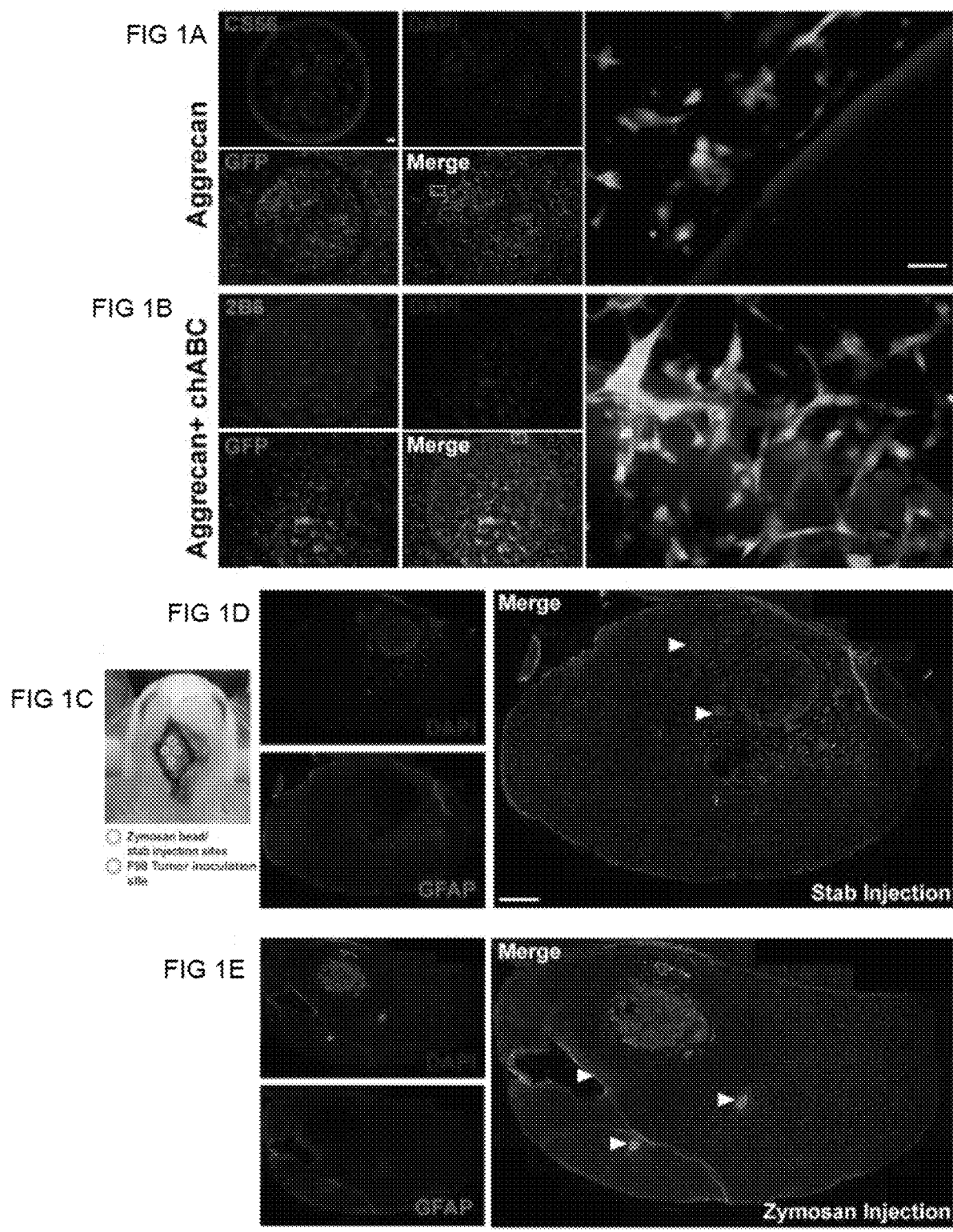
FIG. 1 ((a)-(e)) shows the effects of CSPGs on repelling tumor cells in an established in vitro model of glial scarring.

The present technology is directed to compositions and methods for inducing scarring of peri-tumoral cells to slow the growth of, contain, and/or substantially prevent the spread of cancerous cells from the treatment locus. Several aspects of the technology are directed to compositions and methods for inducing scarring of peri-tumoral cells by targeting and activating peri-tumoral cells with a stimulus that recapitulates the sequelae of a traumatic CNS injury. Such activation of the peri-tumoral cells creates a local barrier or wall around the existing tumor that is impermeable to tumor cells, thereby at least partially restraining invasive tumor growth or spread.

Several aspects of the technology include a composition that compromises (1) a nanoparticle; (2) optionally, a linker and/or a masking agent; and (3) a ligand configured to activate peri-tumoral cells to induce scarring by the peri-tumoral cells. In some aspects, the composition does not include the linker and/or masking agent and only comprises the nanoparticle and the ligand.

In some aspects, the composition may be configured to activate production of chondroitin sulfate proteoglycans (CSPGs), which is a diverse family of covalently linked protein-chondroitin sulfate (CS) glycosaminoglycan (GAG) polysaccharide complexes. Activating production of CSPG may be especially beneficial for slowing or preventing the spread of brain cancer (such as GBM). A critical determinant of brain tumor invasion is its extracellular matrix (ECM). In general, the ECM is a key component in the pathophysiology of nervous system injury. The ECM of the glial scar formed after traumatic brain or spinal cord injury is inhibitory to axonal regeneration. The growth-promoting or inhibitory/repulsive effects of CSPGs are exerted predominantly by the various CS-GAGs that form the CSPGs. CSPG-rich glial scarring around sites of traumatic brain or spinal cord injury provides a critical barrier, quelling inflammation and preventing wider spread of tissue damage by ""walling-off"" the injury site. Additional details regarding the compositions and methods of the present technology are described below.

Nanoparticles

In some aspects, suitable nanoparticles will have an average diameter between about 50 nm-200 nm. In some embodiments, suitable nanoparticles will be configured to leverage the EPR effect to target and accumulate in the tumor periphery of vascularized tumors such as GBM.

In some aspects, the nanoparticles are gold nanoparticles. Gold nanoparticles are known to optimize the biodistribution of drugs to diseased organs, tissues, and cells, in order to improve and target payload delivery. Nanoparticles are particularly useful for difficult delivery sites (brain, retina, tumors, intracellular organelles). The performance of the nanoparticles depends on the size and surface functionality of the particles. Suitable gold nanoparticles are well known, and include colloidal gold Product Nos. 15701-1 through 15714-20 from Ted Pella, Inc. In a specific aspect, a suitable gold nanoparticle may include product No. 15708 (60 nm diameter) purchased from Ted Pella, Inc. In other aspects, any suitable iron, silica or poly(lactic-co-glycolic acid) (PLGA) nanoparticle may be used in combination with or substituted for gold nanoparticles. For example, suitable iron oxide nanoparticles may include Product Nos. 747327, 747424, 747254, 747343, 7476319, 747300, 747408, 747416, 790508, 747335, 747432, 747459, 747467, and 747440 from Sigma Alrdrich, Inc., as well as poly(vinyl alcohol) nanoparticles. Suitable silica microspheres may include, for example, Product No. 24320-15, 24298-10, 24040-10, and 24041-10 from Polysciences, Inc. Suitable PLGA nanoparticles may include, for example, Degradex® Product Nos. 805092 and 805106 from Sigma Aldrich, Inc.

In another aspect, the nanoparticle may comprise a liposome. ""Liposomes,"" as used herein, generally refer to spherical or roughly spherical particles containing an internal cavity. The walls of liposomes can include a bilayer of lipids. These lipids can be phospholipids. Numerous lipids and/or phospholipids may be used to make liposomes. One example are amphipathic lipids having hydrophobic and polar head group moieties, which may form spontaneously into bilayer vesicles in water, as exemplified by phospholipids, or which may be stably incorporated into lipid bilayers, with their hydrophobic moiety in contact with the interior, hydrophobic region of the bilayer membrane, and their polar head group moiety oriented toward the exterior, polar surface of the membrane. In some aspects, suitable liposomes may include those disclosed in U.S. Pat. No. 7,785,568, the entire contents of which are incorporated herein by reference.

Linkers and Masking Agents

The linker may be any compound that will associate the nanoparticle with the targeting ligand. In some aspects, the linker may form a covalent bond to the nanoparticle, the ligand, or both. In some aspects, interactions between the linker and either the nanoparticle, ligand, or both are non-covalent (e.g., hydrogel bonds, affinity, etc.). More generally, the linker may be a molecule that has a functional group at each end with which the linker binds the ligand to the body of the nanoparticle. The linker may be cleavable or non-cleavable. The linker may also be a part of the ligand; in that case, the ligand may be connected to the nanoparticle directly.

In some aspects, the conjugate may comprise a masking agent that protects the particles from being scavenged by the immune system as well as associating with the nanoparticle and ligand. In some aspects, the linker and/or masking agent may be a polymer. In a specific aspect, the linker and/or masking agent may be PEG, a PEG derivative, or a hydrophilic polycarbonate. The polymer can have any of a variety of molecular weights. In one example, the polymer comprises PEG and the PEG chain has a molecular weight between about 1,000-10,000 Da.

Ligands

In some aspects, suitable ligands include any ligands that will: (i) form a conjugate with, be encapsulated by, or otherwise associate with the nanoparticle; and (ii) are configured to activate peri-tumoral cells to induce scar deposition by the peri-tumoral cells.

In one aspect, suitable ligands include those configured to target at least one of the following entities in peri-tumoral cells: (i) TLR2 receptor; (ii) TLR4 receptor; (iii) CSF-1 receptor; (iv) IFN-gamma receptor 1; (v) IFN-gamma receptor 2; (vi) xylosyltransferase; (vii) TNF-alpha receptor; and (viii) IL-2 receptor.

In yet another aspect, the ligand is selected from one or more of peptidoglycan, LPS, zymosan, Pam3CSK4, amyloid-beta peptide, lipoteichoic acid, HMGB1, heat shock proteins, CSF-1R inhibitors, LPS+IFN-gamma, xyloside, IFN-gamma, TNF-alpha, IL-2, lipocalin 2, and miRNA-155. The term ""ligand"" further includes extracts thereof. For example, the ligand may comprise a zymosan extract (Zpep) that is both water soluble and comprises a protein fraction. Preferably, the extract comprises a protein fraction in sufficient amounts to provide a concentration of about 25 μg/mL in an application. The protein fraction may comprise any proteins routinely found in zymosan. The protein fraction may comprises proteins, protein fragments, polypeptides, or a combination thereof.

Zymosan, a yeast cell wall preparation, specifically activates microglia and astrocytes when injected directly into the brain, recapitulating the sequelae of a physical injury in its absence. Microglial-conditioned medium, and not the direct addition of Zpep, activated astrocytes, indicating that Zpep exerted its inflammatory effects via macrophages and perhaps other myeloid cells in vivo. Thus, the term ""induce"" may mean to directly cause, and it may mean to activate endogenous processes that, in turn, cause the desired effect.

By ""targeting molecule,"" what is meant is a compound that serves to target or direct the ligand to a particular location or cell type. In general, the targeting molecule specifically binds a specific target epitope or receptor. ""Specifically binds"" means that non-target cells either do not specifically interact with the ligand or are only poorly recognized by the ligand. In some aspects, the targeting molecule is all or a portion (e.g., a binding portion) of a ligand for a cell surface receptor. Suitable ligands include, but are not limited to, all or a functional portion of the ligands that bind to a cell surface receptor.

By ""entities"" in a peri-tumoral cell, what is meant is any moiety within or on the surface of a cell. The entity may be a cell surface receptor or any molecule that interacts with the appropriate ligand. Alternatively, the entities may be described as on a peri-tumoral cell as well as embedded within the cellular membrane of a peri-tumoral cell.

By ":peri-tumoral"" what is meant is any cell that is in the near vicinity of a tumor. The cells may be immediately adjacent to a tumor, may be in contact with the tumor, or may be near the tumor.

By ""induce scarring by the peri-tumoral cell,"" or iterations thereof, what is meant is that exposure of any peri-tumoral cell to the compositions described herein begins a process whereby a scarring process occurs. This process results in a wall between a tumor and healthy tissue. The wall is generated by the induced peri-tumoral cell and may include the peri-tumoral cell and other components.

The enhanced permeability and retention (EPR) effect describes the preferential accumulation of nanoparticles within tumors owing to their leaky vasculature (enhanced permeation) and poor lymphatic drainage (retention). As nanoparticles shielded from the immune system traverse through the bloodstream, every time they pass through the leaky tumor vasculature, they leak out of the blood vessels into the tumor, and over time—with multiple passes, they accumulate in the tumor. The particles are retained in the tumor due to the poor lymphatic and vascular drainage of the tumor, until they are phagocytosed by other phagocytic cells, or dissolved/disintegrated, or until mature vasculature or lymphatic drainage in the tumor is established.

In another aspect, methods are provided for the preparation of the conjugates and encapsulates provided herein.

In still another aspect, methods are provided for activating peri-tumoral cells to induce scarring by the peri-tumoral cells. In one aspect, the method comprises administering a nanoparticle composition to target cells in close proximity to tumors in order to activate the cells and stimulate scarring. In one aspect, the method comprises administering gold nanoparticles coated with polypeptides to target stromal cells in close proximity to GBM tumors in order to activate the cells and stimulate stromal CSPG expression.

In one aspect, compositions and methods are provided for leveraging endogenous mechanisms of scar formation to moderate tumor growth by modulating the behavior of cells other than those of the tumor. In a specific aspect, compositions and methods are provided for targeting of endogenous mechanisms for induced inhibitory CSPG expression in the stromal space using the EPR effect via gold nanoparticles.

In one aspect, methods are provided for tumor containment. In a specific aspect, the method for tumor containment relies partly on the activation of astrocytes, microglia, and/or the production of CSPGs.

For the purposes of promoting an understanding of the principles of the present disclosure, reference has been made to specific, enabling aspects. For instance, the aspects described herein are directed primarily to the administration of gold nanoparticles coated with Zpep to target stromal cells in close proximity to GBM tumors in order to activate the cells and stimulate stromal CSPG expression. However, no such limitation of the scope of the disclosure is intended. Rather, the inventors contemplate the use of each of the nanoparticle-ligand combinations disclosed herein for targeting to any peri-tumoral cells to induce scarring and, thus, tumor containment.

Articles ""a"" and ""an"" are used to refer to one or to more than one (i.e., at least one) of the grammatical object of the article. By way of example, "an element" means at least one element and can include more than one element.

""About"" is used to provide flexibility to a numerical range endpoint by providing that a given value may be ""slightly above"" or ""slightly below"" the endpoint without affecting the desired result.

The use herein of the terms ""including,"" ""comprising,"" or ""having,"" and variations thereof, is meant to encompass the elements listed thereafter and equivalents thereof as well as additional elements. Aspects recited as ""including,"" ""comprising,"" or ""having"" certain elements are also contemplated as "consisting essentially of" and "consisting of" those certain elements. As used herein, ""and/or"" refers to and encompasses any and all possible combinations of one or more of the associated listed items, as well as the lack of combinations where interpreted in the alternative (""or"").

As used herein, the transitional phrase ""consisting essentially of"" (and grammatical variants) is to be interpreted as encompassing the recited materials or steps "and those that do not materially affect the basic and novel characteristic(s)" of the claimed invention. See In re Herz, 537 F.2d 549, 551-52, 190 U.S.P.Q. 461, 463 (CCPA 1976) (emphasis in the original); see also MPEP § 2111.03. Thus, the term "consisting essentially of" should not be interpreted as equivalent to ""comprising.""

Moreover, the present disclosure contemplates that in some aspects, any feature or combination of features can be excluded or omitted. To illustrate, if the specification states that a complex comprises components A, B, and C, it is specifically intended that any of A, B, or C, or a combination thereof, can be omitted and disclaimed singularly or in any combination.

Recitation of ranges of values are merely intended to serve as a shorthand method of referring individually to each separate value falling within the range, unless otherwise stated, and each separate value is incorporated into the specification as if it were individually recited. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms have the same meaning as commonly understood by one of ordinary skill in the art to which this disclosure belongs.

As used herein, ""treatment,"" ""therapy,"" and ""therapy regimen"" refer to the clinical intervention made in response to a disease, disorder, or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder, or condition. The aim of the treatment may include slowing the progression of cancerous tissue, increasing the susceptibility of the cancerous tissue to more conventional treatments or reducing the side effects of chemotherapy and/or radiation therapy directed at the cancerous tissue. The term "effective amount" or "therapeutically effective amount" refers to an amount sufficient to effect beneficial or desirable biological and/or clinical results.

The term ""disease"" as used herein includes, but is not limited to, any abnormal condition and/or disorder of a structure or a function that affects a part of an organism. It may be caused by an external factor, such as an infectious disease, or by internal dysfunctions, such as cancer, cancer metastasis, and the like.

""Administration"" as it applies to a human, primate, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition (e.g., a gold nanoparticle:linker:ligand conjugate as provided herein) to the subject, cell, tissue, organ, or biological fluid, and the like.

As is known in the art, a cancer is generally considered as uncontrolled cell growth. The methods of the present aspects can be used to affect the peri-tumoral tissue surrounding any cancer, and to impede or prevent any metastases/migration thereof. In some aspects, the cancer comprises a solid tumor. Examples include, but are not limited to, breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulval cancer, pancreatic cancer, thyroid cancer, hepatic carcinoma, skin cancer, melanoma, uveal melanoma, brain cancer (e.g., GBM), neuroblastoma, various types of head and neck cancer, Ewing sarcoma, peripheral neuroepithelioma, adrenocortical cancer, rectal cancer, esophageal cancer, thyroid cancer, stomach cancer, mesothelioma, testicular cancer, and the like, including both primary and metastatic.

As used herein, the term ""subject"" and ""patient"" are used interchangeably herein and refer to both human and nonhuman animals. The term ""nonhuman animals"" of the disclosure includes all vertebrates, e.g., mammals and non-mammals, such as nonhuman primates, sheep, dog, cat, horse, cow, chickens, amphibians, reptiles, and the like.

The compositions described herein can be administered to a subject, either alone or in combination with a pharmaceutically acceptable excipient, in an amount sufficient to induce an appropriate response. The response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression. In some aspects, the response comprises the activation of stromal cells to produce CSPGs.

In some aspects, the present disclosure provides a method for providing a treatment in a subject by administering to the subject an effective amount of proteoglycan. An ""effective amount,"" as used herein means an amount that provides a therapeutic or prophylactic benefit. Effective amounts of the conjugates or encapsulates as provided herein can be determined by a physician with consideration of individual differences in age, weight, tumor size, extent of infection or metastasis, and condition of the patient (subject). It can generally be stated that a pharmaceutical composition comprising the conjugates or encapsulates described herein may be administered at a dosage of 1 to $10^{11}$ particles/kg body weight, preferably 2 to $10^{10}$ particles/kg body weight, including all integer values within those ranges. Conjugates or encapsulates may also be administered multiple times at these dosages. The conjugates or encapsulates can be administered by using techniques that are commonly known in the art, including intravenous, intratumoral, subcutaneous, and intraperitoneal administration. The optimal dosage and treatment regime for a particular patient can readily be determined by one skilled in the art of medicine by monitoring the patient for signs of disease and adjusting the treatment accordingly.

An effective amount of the conjugates or encapsulates described herein may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more administrations of the composition. Where there is more than one administration in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term ""about"" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof, including several weeks or even months between administrations. The invention is not limited to dosing intervals that are spaced equally in time, but encompass doses at non-equal intervals, such as a priming schedule consisting of administration at 1 day, 4 days, 7 days, and 25 days, just to provide a non-limiting example.

A ""pharmaceutically acceptable excipient"" or ""diagnostically acceptable excipient"" includes but is not limited to, sterile distilled water, saline, phosphate buffered solutions, amino acid-based buffers, or bicarbonate buffered solutions. An excipient selected and the amount of excipient used will depend upon the mode of administration. Administration comprises an injection, infusion, or a combination thereof.

An effective amount for a particular subject/patient may vary depending on factors such as the condition being treated, the overall health of the patient, the route and dose of administration, and the severity of side effects. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

The conjugates and encapsulates of the present disclosure can be administered in a dose, or dosages, where each dose comprises at least 100 conjugates or encapsulates/kg body weight or more; in certain aspects 1000 conjugates or encapsulates/kg body weight or more; normally at least 10,000 conjugates or encapsulates; more normally at least 100,000 conjugates or encapsulates; most normally at least 1 million conjugates or encapsulates; often at least 10 million conjugates or encapsulates; more often at least 100 million conjugates or encapsulates; typically at least 1 billion conjugates or encapsulates; usually at least 10 billion conjugates or encapsulates; conventionally at least 100 billion conjugates or encapsulates; and sometimes at least 1 trillion conjugates or encapsulates/kg body weight.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non-dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

The conjugates and encapsulates according to the present disclosure may also be administered alongside one or more therapeutic/anti-cancer agents/therapies. Methods for co-administration with a therapeutic/anti-cancer agents/therapies are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.).

Co-administration need not refer to administration at the same time in an individual, but rather may include administrations that are spaced by hours or even days, weeks, or longer, as long as the administration of multiple therapeutic agents is the result of a single treatment plan. The co-administration may comprise administering the conjugates and encapsulates of the present disclosure before, after, or at the same time as the alternative agents/therapies. In one treatment schedule, the conjugates and encapsulates of the present disclosure may be given as an initial dose in a multi-day protocol, with alternative agents/therapies given on later administration days; or the alternative agents/therapies given as an initial dose in a multi-day protocol, with the conjugates or encapsulates of the present disclosure given on later administration days. On another hand, alternative agents/therapies and the conjugates and encapsulates of the present disclosure may be administered on alternate days in a multi-day protocol. This is not meant to be a limiting list of possible administration protocols.

Yet another aspect of the present disclosure provides a method of reducing and/or preventing the migration of a cancer in a subject, the method comprising, consisting of, or consisting essentially of administering to the subject a therapeutically effective amount of a conjugate or encapsulate as provided herein such that the migration of the cancer is reduced and/or prevented.

In some aspect, the methods further comprise administering to the subject an anti-cancer therapy. In some aspects, the anti-cancer therapy is selected from the group consisting of radiation, chemotherapy, immunotherapy, surgery, hormonal therapy, target therapy, synthetic lethality, induced tumor migration, immunotherapy, and combinations thereof.

In some aspects, such compositions and methods may complement adjuvant interventions, such as radiation, chemotherapy, surgery, hormonal therapy, target therapy, synthetic lethality, designed tumor migration such as that described in U.S. application Ser. Nos. 13/814,009 and 16/432,475, the entire contents of which are incorporated herein by reference, immunotherapy, and combinations thereof, for invasive tumors, such as invasive GBM.

The following Examples are provided by way of illustration and not by way of limitation.

EXAMPLES

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed aspects.

Methods

Cell Lines and Culture Procedures. U87 cells (human glioma, HTB-14), F98 cells (Fischer rat glioma, CRL-2397), EOC cells (mouse microglia, CRL-2469), LADMAC cells (mouse macrophages/monocytes, CRL-2420), and C8D1A cells (mouse cerebellum astrocytes, CRL-2541) were purchased from ATCC and maintained according to instructions specific to each cell line. The CRL-2469 cell line was cultured in Dulbecco's Modified Eagle Medium (DMEM; Corning) and 10% FBS with either 30 ng ml-1 recombinant mouse CSF-1 (416-ML-010, R&D Systems) or with conditioned medium from LADMAC cells. All cells were grown at 37° C. with 5% $CO_2$, passaged with trypsin-EDTA 0.05% and maintained in respective complete cell culture medium (ATCC recommended) and 1% penicillin-streptomycin (Gibco) unless otherwise noted. As noted for some experiments, U87 cells were made to stably express enhanced green fluorescent protein (eGFP), via transfection with an eGFP expression plasmid using the Effectene Transfection Reagent (Qiagen) and further selection of stable transfectants with G418 Sulfate (Gemini).

Spot assays. Preparation of 14-mm glass-bottomed Petri-dishes (In vitro Scientific, Sunnyvale, CA) was done according to known methods with few modifications. Briefly, surfaces were coated with poly-L-lysine (PLL, 1:10 dilution in ultrapure water) (Sigma-Aldrich) and incubated overnight at 37° C. The following day, the surfaces were rinsed thrice with sterile water and allowed to dry completely. Various concentrations of aggrecan, bovine serum albumin (BSA), and fibronectin with Texas Red (Invitrogen) were spotted onto the prepared surfaces in 2 µL amounts and allowed to dry completely. 80,000 U87 mg cells (stably expressing eGFP) suspended in standard growth medium were carefully added to the chambers. After 24 hours, the cells were fixed with 4% paraformaldehyde and 0.4M sucrose solution for 15 min and immunostained for CS-56 (Sigma C8035, 1:250).

For determining the effect of GAG side chains, aggrecan spots were treated extensively with cABC (1 U/mL; 3-5 h, 37° C.; Sigma). After aspirating the cABC and rinsing with PBS, 80,000 eGFP+U87 mg cells were plated as described above. After 24 h, cells were fixed and immunostained for 2B6 (Seikagaku, 1:250) and CS-56 (1:200).

Zpep extraction. Zymosan (Sigma Aldrich, 250 mg) was snap frozen in liquid nitrogen and crushed into a fine powder using a mortar and pestle. The crushed zymosan was added to an extraction buffer (10 mL) containing TRIS—HCl (0.5 M), CHAPS (1%), DTT (1%), and PMSF. The extraction process was allowed to go on overnight at room temperature (rt) with gentle agitation. The next day, the samples were centrifuged at 5000×g for 10 min and the supernatant was collected, following which it was washed, concentrated, and dialyzed (3×) using a 10 kDa centrifugal spin column (EMD Millipore, Amicon Ultra-15) according to the manufacturer's instructions. Protein concentrations were determined using a NanoDrop device. Zpep aliquots were stored at −20° C. until further use.

In vitro experiments. Zpep was used at a concentration of 25 µg/mL in vitro. Nitrite production was assessed at time points (indicated in figure legends) using the Griess reagent system (G2930, Promega). TLR2 blocking experiments were performed as known in the art. TNF-α levels were assessed using anti-TNF-α enzyme-linked immunosorbent assay (ELISA) kit as per the manufacturer's instructions (BD Biosciences, RayBiotech). Quantitative real-time PCR was performed on a multiplexed Fluidigm system, and data were analyzed according to known methods. Primers were purchased from Fluidigm Inc.

Gold nanoparticle conjugates (AuNP—Z). Gold nanoparticles (AuNPs) were purchased from Ted Pella, Inc. (60 nm diameter, 15708-6). PEG-thiol (MPEG-SH-20K-1 g) was purchased from Laysan Bio. All reactions were performed in ultrapure DI water (18 MΩ cm-1). The amount of AuNPs each animal received per dose was 57 microgram (=1 ml of 60 nm AuNPs, at a concentration of $2.6 \times 10e^{10}$ particles/ml). PEG-SH concentration was calculated such that each AuNP received 30,000 PEG-SH molecules. Zpep and PEG-SH were conjugated to AuNPs as follows: PEG was dissolved in ultrapure DDI water. Zpep was reconstituted at 1 mg/ml, such that each animal would receive 100 microgram final dose (based on initial concentration of zymosan and assuming 100% conjugation efficiency). Zpep was suspended in 3 mM Tris base buffer. AuNPs were centrifuged (12000×g, 20 min) and re-suspended in ultrapure DDI water. The AuNPs, PEG-SH, and Zpep were combined and left on a rotating test-tube holder overnight at rt. Particles were aliquoted into individual doses and washed twice by centrifugation (12,000×g, 20 min) before being re-suspended in sterile saline for in vivo tail vein injections, or ultrapure DDI water for physical characterization. Dynamic light scattering and UV-Vis spectroscopy were performed by known techniques.

Tumor inoculation. All experiments were approved by the Institutional Animal Care and Use Committee at the Georgia Institute of Technology and Duke University. Rowett nude rats or Fischer rats (175-200 g, male, Charles River Laboratories) were inoculated with U87 mg (80,000 cells) or F98 tumor cells (10,000 cells), respectively. The animals were anesthetized using 5% isoflurane and maintained with 2-3% isoflurane during surgical procedures. The animals were placed in a stereotaxic device. A 1 cm incision was made on the head. The periosteum was cut and removed from the skull. A hole was made in the skull 2 mm lateral and 2 mm posterior from bregma. A 26-gauge needle mounted on a 10 µL Hamilton syringe was inserted 2 mm deep from the surface of the brain and retracted 0.5 mm. Tumor cells in 5 µL of DMEM (serum-free) were injected using an automated syringe pump at a rate of 1 uL/minute. The needle was held in place an additional 2 min before removal and closing. Animals displaying symptoms of distress from the glioblastoma were anesthetized with ketamine (1 mL/kg), xylazine (0.17 mL/kg), and acepromazine (0.37 mL/kg), transcardially perfused with physiological PBS, followed by 4% paraformaldehyde. The brains were dissected and incubated in 4% paraformaldehyde overnight, and were stored in 30% sucrose containing 0.01% sodium azide. For cohorts designated to proteomics and histology, anesthetized animals were transcardially perfused with physiological PBS followed by 10% formalin, and stored in 10% formalin at rt (i.e. room temperature).

MRI Imaging. Rats were anaesthetized and placed in a Bruker Pharmascan 7-T (Bruker BioSpin MRI) operating with the ParaVision software with a 38-mm quadrature-detection volume coil as head coil. The animals were anaesthetized using 2% isoflurane and placed in a home-built cradle, allowing the easy placement of the animals' heads within the MRI coil. The rapid acquisition of high quality T2 weighted images was achieved using the rapid imaging with refocused echoes (RARE) sequence (RARE factor, 6; effective echo time, 36 ms; repetition time [TR], 4,200 s; two averages per scan; total acquisition time, 6 min). A slab of 40 transversal slices was recorded using a field of view of 40 mm×40 mm with a 256×256 matrix and a slice thickness of 0.5 mm. This slab was aligned to cover the injection site of the tumor cells using a pilot scan, which was recorded immediately before the acquisition of the RARE images. MR images were acquired roughly every week following tumor implant to check for tumor growth or regression. ImageJ software (FIJI, version 2.0) was used for further image processing, and for tumor volume calculations. A region of interest (ROI) following the tumor borders was drawn manually in the T2-weighted images. The whole tumor volume was calculated by adding up the voxel volumes within the ROIs of all image slices. In the case that MRI was not possible on days of euthanasia, tumor volume at time of death was extrapolated assuming a linear tumor growth rate.

Proteomics at Duke proteomics and metabolomics shared resource. U87 mg tumors that had previously been fixed in formalin were macro-dissected from the surrounding normal tissue from the brains of 9 rats: 3 different animals per group, 3 groups total. The wet weight of each was noted. 1 mL of 50 mM ammonium bicarbonate (AmBic) was added to each tumor, and heated at 80° C. for 55 min while shaking at 750 rpm. The AmBic was removed, and another 1 mL of AmBic was added for a second rinse. The second rinse was then pipetted off, and the tumor was allowed to cool completely at room temperature (<5 min). Each tumor was transferred to a centrifuge tube, and 8 M urea in 50 mM AmBic was added at 10 µL per mg of wet weight. The tissue was then taken through tissue tearing until no tissue pieces were visible, and the samples were homogenized. The samples were then probe sonicated at power level 3 for 5 s bursts, 3 bursts each while on ice. A concentration was determined for each homogenate by Bradford assay. 50 µg from each sample was taken out and concentration normalized in 8 M urea in 50 mM AmBic. Then, enough AmBic was added to each to get to 1.8 M urea for subsequent in-solution tryptic digestion. The samples were reduced in 10 mM dithiothreitol (DTT) at 32° C. for 45 min, alkylated in 25 mM iodoacetamide (IAA) at rt in the dark for 30 min, and trypsin was added to each at a 1:50 ratio of enzyme to protein for digestion at 32° C. overnight while shaking at 750 rpm. The following morning, the samples were acidified with trifluoroacetic acid to give 0.5% TFA final, and taken through a C18 SPE cleanup (Waters Sep-Pak Vac, 50 mg cartridges, Product #WAT054955). After some of the acetonitrile was evaporated via Speed Vac, the remaining extracts were taken to dryness by lyophilization overnight. The samples were then reconstituted in 200 µL of 1% TFA/2% ACN containing 25 µmol/µL yeast alcohol dehydrogenase surrogate standard. A QC pool was prepared by mixing equal volumes of all samples.

Quantitative Mass Spectrometry. Quantitative one-dimensional liquid chromatography, tandem mass spectrometry (1D-LC-MS/MS) was performed on the peptide digests per sample, with additional analyses of conditioning runs and QC pools. Samples were analyzed using a nanoACQUITY UPLC system (Waters) coupled to a QExactive Plus high resolution accurate mass tandem mass spectrometer (Thermo) via a nanoelectrospray ionization source. The sample was trapped on a Symmetry C18 180 µm×20 mm trapping column (5 µL/min at 99.9/0.1 v/v H2O/MeCN), followed by an analytical separation using a 1.7 m Acquity HSS T3 C18 75 m×250 mm column (Waters) with a 90 min gradient of 5 to 40% MeCN/H2O with 0.1% formic acid at a flow rate of 400 nL/min and column temperature of 55° C. Data collection on the QExactive Plus MS was performed in data-dependent acquisition mode with a 70,000 resolution (@ m/z 200) full MS scan from m/z 375 to 1600 with a target AGC value of 1e6 ions followed by 10 MS/MS scans at 17,500 resolution (@ m/z 200) at a target AGC value of 5e4 ions. A 20-s dynamic exclusion was employed. The total analysis cycle time per sample injection was approximately 2 h. Following 12 total UPLC-MS/MS analyses (including 3 replicate QC injections), data were imported into Rosetta Elucidator v 4.0 (Rosetta Biosoftware, Inc.), and analyses were aligned based on the accurate mass and retention time of detected ions (""features"") using PeakTeller algorithm in Elucidator. Relative peptide abundance was calculated based on area-under-the-curve (AUC) of the selected ion chromatograms of the aligned features across all runs. Elucidator was utilized to produce fragment ion spectra, and Mascot Server (v 2.5, Matrix Sciences) performed the database searches. The MS/MS data were searched against two databases: a Swissprot database with *Homo sapiens* taxonomy and a NCBI refseq database with *Rattus norvegicus* taxonomy (both downloaded in August 2016) with additional proteins commonly used as internal controls including yeast ADH1, bovine serum albumin, and bovine alpha casein, as well as an equal number of reversed-sequences (""decoys"") for false discovery rate determination. Database search parameters included fixed modification on Cys (carbamidomethyl) and variable modifications on Asn and Gln (deamidation) and Met (oxidation), 2 missed cleavages, precursor tolerance of 5 ppm and product tolerance at 0.2 Da, and trypsin as the enzyme specificity. After individual peptide scoring using the PeptideProphet algorithm in Elucidator, the data were annotated at a 0.9% peptide false discovery rate.

Proteomic Differential Expression. For proteomics, comparisons between fold changes of the protein-level intensities (PLIs) were used to determine proteins that were differentially expressed (DE) between the conditions (Z: AuNP—Z; P: AuNP—P; C: control, no AuNP; n=3). The statistical comparison tool QPROT (v1.3.3)72 (nburnin: 2,000; niters: 10,000; normalized: true) was used to compute a z-statistic and FDR for each identified protein compared pairwise between conditions. The p values were obtained from the z-statistic using Python (Version 2.7.11, Anaconda 2.2.0; https://www.python.org/). Proteins with a FDR<0.05 for a particular fold change comparison between conditions were considered statistically significant and treated as DE for that condition-pair.

Pathway Overrepresentation Analysis. The DE proteins were pre-filtered to exclude proteins with an absolute fold change of less than 2-fold. For each condition-pair, gene ontology was performed using g:profiler version: rl730_e88_eg35 (http://biit.cs.ut.ee/gprofiler/). Both *Rattus norvegicus* and *Homo sapiens* datasets were used. Since parsimonious assignment of species is unreliable for closely homologous proteins, each species dataset was run for all proteins (species-indifferent), as well as the subsets of proteins identified as either rat or human. The search included Gene Ontology, KEGG, Reactome, and Regulatory Motif databases and used the built-in g:SCS threshold for significance. Default settings were used. QuickGO (https://www.ebi.ac.uk/QuickGO) web service was used for obtaining additional gene ontology information for visualization with Python.

Pathway Enrichment Analysis. Gene Set Enrichment Analysis (GSEA) Release 3.0 (http://www.broadinstitute.org/gsea) was used to perform pathway enrichment analysis. Pre-ranked analysis was performed against the curated (c2.all.v6.0), and gene ontology (c5.all.v6.0), datasets using the negative-log of the QPROT p-value, signed according to fold-change direction, as the ranking scheme for each condition-pair. The isoform with the lowest p-value was selected in cases of gene symbol collision. Default settings were used except the max and min pathway size exclusion criteria were set to 1,000 and 5, respectively.

Immunohistochemistry, immunofluorescence, and microscopy. All antibodies used for IHC and IF are listed in Figure Captions. Fixed, frozen brain tissue was sectioned to 14-μm thickness, and prepared for immunofluorescence using known methods. Sections were imaged on a Zeiss Axiovision inverted microscope. For IHC, tissues were processed at the Emory Winship Pathology Core Lab, using known methods. Tissues from paraffin-embedded blocks were sectioned at 5-μm thickness. IHC was performed using DAB chromogenic kit (Wako) following the manufacturer's protocol. Whole-slide scanning was done using a Hamamatsu Nanozoomer 2.0 HT.

Graphing and Statistics. All graphs were made in Prism 7 (Graphpad Inc.), Python, or MATLAB (Version 9, Mathworks, MA). Layout of figure panels was done with Illustrator (Adobe Inc.). Outliers were omitted when indicated by a Grubb's test. Where appropriate, Student's t-tests or one-way ANOVA (as described in figure legends), followed by post-hoc tests were run in Prism 7. Survival analysis was also performed in Prism 7, and significance was assessed using the Mantel-Cox log rank test.

Example 1

Using CSPGs to repel GBM cells (FIG. 1(a)-(e)). To determine the effects of CSPGs on repelling tumor cells, an established in vitro model of glial scarring was used, namely, spot assay using a prototypical inhibitory CSPG, aggrecan. Aggrecan was chosen because it is a constituent of glial scars, and is sulfated with all of the families of CS-GAGs. The results are shown in FIG. 1(a) (scale bar is 50 μm). U87 mg GBM cells expressing green fluorescent protein (GFP) were used. ""DAPI"" indicates the nuclear stain 4',6-Diamidino-2-Phenylindole, and "CS56" is an antibody that stains intact CSPGs. A spot of CS56+ aggrecan (1 mg/ml, 2 ul spot) repels the tumor cells: The dotted line (""Merge"") identifies the zoomed-in region (scale bar is 200 μm) on the far right, confirming that tumor cells are at least partially prevented from crossing the boundary posed by aggrecan.

Since CSPGs exert their inhibitory effects primarily via the CS-GAG side chains, chondroitinase ABC (cABC) was used to enzymatically digest and cleave the CS-GAG chains to determine whether the boundary was sustained in the absence of CS-GAG side chains. The results are shown in FIG. 1(b). 2B6 is an antibody that stains the GAG stubs following enzymatic digestion of aggrecan by chondroitinase ABC (chABC). Tumor cells were able to cross the spot boundary posed by aggrecan upon chABC digestion, indicating that CSPGs mediate their repulsive effects via CS-GAGs, and confirming that CSPGs—the principal inhibitory components of the glial scar-contributed a biochemical barrier to the invasion of GBM cells in vitro.

To stimulate peri-tumoral expression of CSPGs, Fischer rats were co-injected with highly motile, syngeneic F98 GBM cells and zymosan. FIG. 1(c) shows the zymosan bead/stab injection sites and the F98 tumor inoculation site. Animals were sacrificed 21 days after tumor inoculation.

F98 tumor cells were excluded from regions of control stabs, as shown in FIG. 1(d). Glial fibrillary acidic protein (GFAP) is an immunofluorescent stain for reactive astrocytes. Stab wounds (indicated by white arrow heads) partially repelled tumor growth, but were unable to prevent tumor microsatellite migration (indicated by red arrow heads). In contrast, zymosan beads caused fulminant gliosis and cavitation (white arrow heads) and caused tumors to remain as compact masses, as shown in FIG. 1(e) (zoomed-in section scale bar is 200 μm). In control animals, tumors formed microsatellites away from stab sites, and in animals treated with zymosan beads, tumor cells were constrained within the boundaries of the bead injection sites. Zymosan injection caused robust astroglial activation, indicating that astroglial scarring largely contained and constrained tumor cell migration in vivo.

Example 2

Using Zpep to activate TLR2 (FIG. 2(a)-(f)). Direct injection of zymosan into brain tumors is not practical for multiple reasons, e.g., risk of injury due to intracranial injections and incomplete coverage of tumor periphery. Nanoparticles bearing zymosan are ideal to obviate these issues, since nanoparticles leverage the EPR effect to target vascularized tumors such as GBM, and accumulate in the tumor periphery—a location ideal for constraining tumors. Thus, a water-soluble mixture comprising zymosan polypeptides (Zpep) was extracted from zymosan beads. Addition of Zpep to EOC mouse microglial cells caused nitric oxide production (assessed by a nitrite assay), which increased with time (Griess assay, FIG. 2(a)), and TNF-α production (FIG. 2(b)). Since zymosan is a TLR2 stimulus, Zpep activation of TLR2-related pathways was determined. Zymosan recognition by mammalian cells is mediated by TLR2 and the β-glucan receptor dectin. EOC cells were treated with laminarin (a soluble β-glucan that can block dectin-mediated recognition) or TLR2-blocking antibody prior to exposure to Zpep. The blocking of TLR2, but not dectin, led to a decrease in nitric oxide production by EOC cells, indicating that Zpep retains the TLR2-activating properties of zymosan (FIG. 2(c)), and that the Zpep extract did not contain any water-insoluble β-glucans. Addition of Zpep to EOC cells caused robust upregulation of genes associated with microglial activation, i.e., inflammatory gene transcripts (FIG. 2(d)). Additionally, Zpep mimics the expected response of zymosan on astrocytes—that is, zymosan cannot activate astrocytes directly but through secretory factors of microglia exposed to zymosan. These properties were confirmed, as direct addition of Zpep was not able to classically activate C8D1A astrocytes (FIG. 2(e), (f)), yet conditioned media from EOC cells exposed to Zpep, induced robust astrocyte activation, as assessed by nitric oxide production and inflammatory gene upregulation (FIG. 2(e), (f)) ("""CM""" indicates EOC-conditioned medium). Taken together, these data indicate that Zpep displays biological properties similar to zymosan and causes robust inflammation in glial cells.

Example 3

Using AuNPZ to stimulate peri-tumoral CSPG expression in vivo (FIG. 3(a)-(c)). As described herein, the surface of AuNPs (60 nm diameter) were decorated with Zpep and 20 kDa PEG to create inflammatory nanoparticles (AuNP—Z). Conjugation of polypeptides onto AuNP surfaces was assessed by ultraviolet-visual spectroscopy. As shown in FIG. 3(a), addition of PEG alone did not lead to a red-shift (peak absorbance at 535 nm for naked AuNPs and AuNP—P). However, addition of Zpep caused a small red-shift of 4-5 nm (peak absorption at 540 nm for AuNP—Z). Dynamic light scattering of AuNPs (60 nm diameter core) showed an increase in hydrodynamic radius of AuNPs upon addition of PEG (100 nm diameter) and Zpep (90 nm diameter).

To test the capacity of AuNP conjugates to cause peri-tumoral CSPG expression in vivo, F98 glioma-bearing Fischer rats were injected intravenously with Zpep-bearing AuNPs (100 µg of Zpep) at 6 days post tumor inoculation (DPI) and sacrificed at 20 DPI. As shown in FIG. 3(b), control tissue sections (b) from animals bearing F98 tumors, but not receiving any treatment, displayed low astrocyte activation (GFAP staining) and low CSPG production (CS56 staining). Conversely, as shown in FIG. 3(c), sections from Zpep-treated animals demonstrated robust astrocyte activation and CSPG production. (Scale bar: 50 µm.)

Example 4

Using AuNP—Z to constrain tumors in vivo (FIG. 4(a)-(b)). F98 glioma-bearing Fischer rats were injected intravenously with AuNPs at 6 days post tumor inoculation (DPI) and sacrificed at 20 DPI. As shown in FIG. 4(a), tissue sections from animals bearing F98 tumors and receiving only PEG-bearing AuNPs display low astrocyte activation (GFAP staining) and low CSPG production (CS56 staining). As shown in the whole-slide scans of FIG. 4(b), animals receiving AuNP—Z had smaller and more constrained tumors. Tumors are outlined with a red dotted circle. Constrainment is determined as a qualitative assessment of how closely packed the tumor cells are. (Scale bar is 100 µm in FIG. 4(a) and 2 mm in FIG. 4(b).)

Thus, animals given AuNP—Z showed smaller, compact tumors (FIG. 4(b)), similar to that observed with direct injection of zymosan beads (FIG. 1(e)). Immunofluorescent staining of glial fibrillary acidic protein (GFAP), a marker of reactive astrocytes, and CSPGs (CS56 antibody) was weak in control and AuNP—P groups (FIG. 3(b) & FIG. 4(a)). However, CS56 and GFAP immunoreactivity was strong in the AuNP—Z group (FIG. 3(c)) with high reactivity within and at the tumor periphery—a phenomenon reminiscent of non-migratory gliomas. Taken together, these data show that systemic injection of AuNP—Z particles induced elevated CSPG and GFAP expression around brain tumors in vivo, and thus constrained them.

Example 5

Using AuNP—Z to retard and contain tumor growth (FIG. 5(a)-(c)). Rowett nude (RNU) rats bearing xenogeneic U87 tumors were injected intravenously with AuNP, AuNP—PEG, and AuNP—Z, single dosed (SD) or double dosed (DD), starting at 9 DPI. As shown in FIG. 5(a), tumor volume was plotted longitudinally for all five experimental groups. Tumor volumes were calculated from MRI images of animals imaged roughly weekly starting at 9 DPI until death. MRI images were analyzed for growth by outlining the tumor on 0.5 mm slices through tumor-bearing rat brains and calculating the volume (mm3). The timeline of the dosing regime is indicated for the SD and the DD groups. The dashed line indicates median volume at time of death of animals in the Control group. Each dot on the growth curve indicates an MRI session from which the tumor volume was calculated. AuNP—Z administration led to slower growing tumors with significantly smaller volumes in animals receiving AuNP—Z (134±100 mm3 in AuNP—Z SD vs. 311±109 mm3 in Control group) (FIG. 5(a)). A few days after AuNP administration, the tumors seemed to pick up in growth rate (FIG. 5(a)); thus, the initial dose was split equally into two halves and injected into the animals at 9 DPI and 13 DPI. This dosing regimen led to even smaller and slower growing tumors (86±35 mm3 in AuNP—Z DD) in comparison with the single-dose cohort (FIGS. 5(b) & 5(c)). FIG. 5(b) shows box and whisker plots summarizing terminal volumes of the five experimental groups in FIG. 5(a). AuNP—Z administration curtailed tumor growth significantly compared to other groups. FIG. 5(c) shows representative T2-weighted MRI images of the experimental groups at the tumor injection site. Images are shown at 9, 16, and 23 DPI for the same animal. (*p<0.05; one-way ANOVA (Kruskal-Wallis test), followed by the Uncorrected Dunn's post-hoc test.)

Example 6

Figure 6:
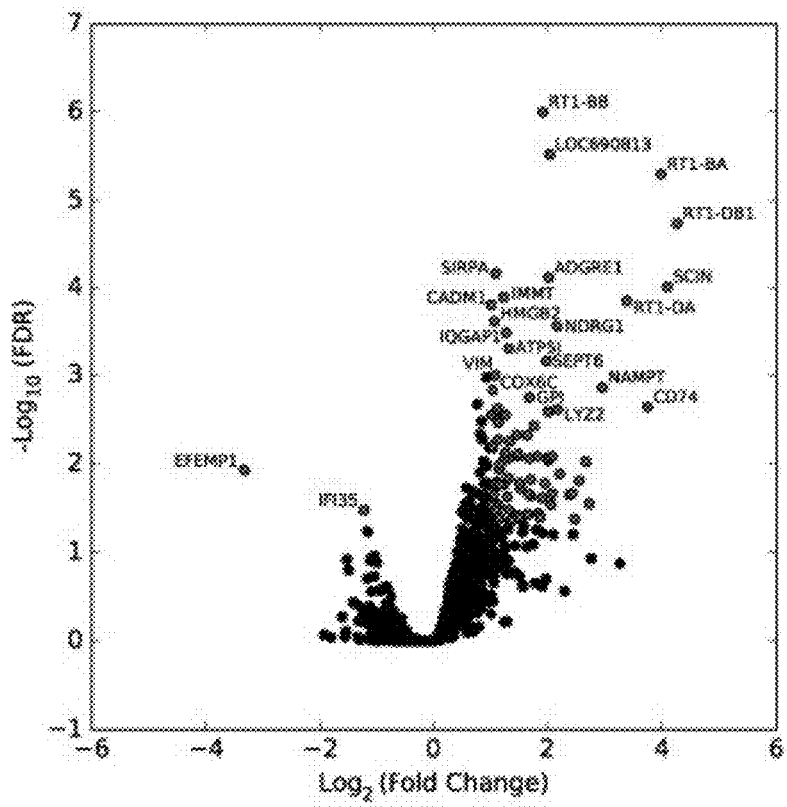
FIG. 6 ((a)-(c)) shows the results of a proteomic analysis of in vivo response to AuNP—Z.

Proteomic analysis of in vivo response to AuNP—Z (FIG. 6(a)-(c)). Proteomic analyses of tumor biopsy showed that AuNP—Z administration led to an increase in proteins involved in cell adhesion, exocytosis, antigen processing, leukocyte-mediated immunity, and extracellular cell structures (FIGS. 6, 7, & 8). In stark contrast, administration of AuNP—PEG particles led to the upregulation of proteins involved in the generation of metabolites, energy derivation, cellular transport, and CNS growth indicating continued tumor progression. Taken together, these data indicate that AuNP—Z administration led to smaller malignant gliomas which was in part mediated by regulation of pathways related to inflammation and cell clustering.

FIG. 6(a) shows a volcano plot depicting differential expression of proteins in AuNP—Z treated animals relative to controls (significantly differentially-expressed proteins are indicated by red dots). Each dot represents a uniquely identified protein accession. Significance threshold was set to a false discovery rate (FDR) of <0.05 and a fold change of greater than +2-fold. These proteins are involved in the pathways listed in FIGS. 6(b) & (c). FIG. 6(b) is a select list of significantly over-represented pathways in the AuNP—Z group relative to controls. FIG. 6(c) is a list of all the significantly enriched pathways in the AuNP—Z group from GSEA analysis. DE refers to differentially expressed, ORA to over representation analysis, and NES to normalized enrichment score.

Example 7

GSEA of proteomic data (FIGS. 7 & 8). GSEA of proteomic data indicated enrichment of pathways related to cytostatic, non-migratory behavior. FIG. 7 shows the results of a gene set enrichment analysis of AuNP—Z-treated animals relative to controls. Pathways and significantly enriched core genes are shown. FIG. 8 shows the results of an overrepresentation analysis of AuNP—Z-treated animals relative to controls. Pathways and significantly differentially expressed core genes are shown. For example, the E-cadherin and MHC class pathways were up-regulated upon AuNP—Z administration in vivo. AuNP—Z administration caused an enrichment of proteins associated with E-cadherin expression. AuNP—Z administration led to enrichment of pathways related to upregulation of MHC class I and II, as well as those related to complement signaling, and Fc-receptor-mediated phagocytosis. Pathways related to cytotoxic and phagocytic functions of microglia require microglia to up-regulated the expression of complement and Fc-gamma receptors. In contrast, animals dosed with AUNP-PEG showed enrichment of pathways related with neuronal cell communication and synaptic transmission, reminiscent of a quiescent microenvironment that allows for tumor growth. Overall, proteomic analysis points toward a mode of action of Zpep that involves regulation of cell adhesion, migration, and immune activation.

Example 8

Figure 9:
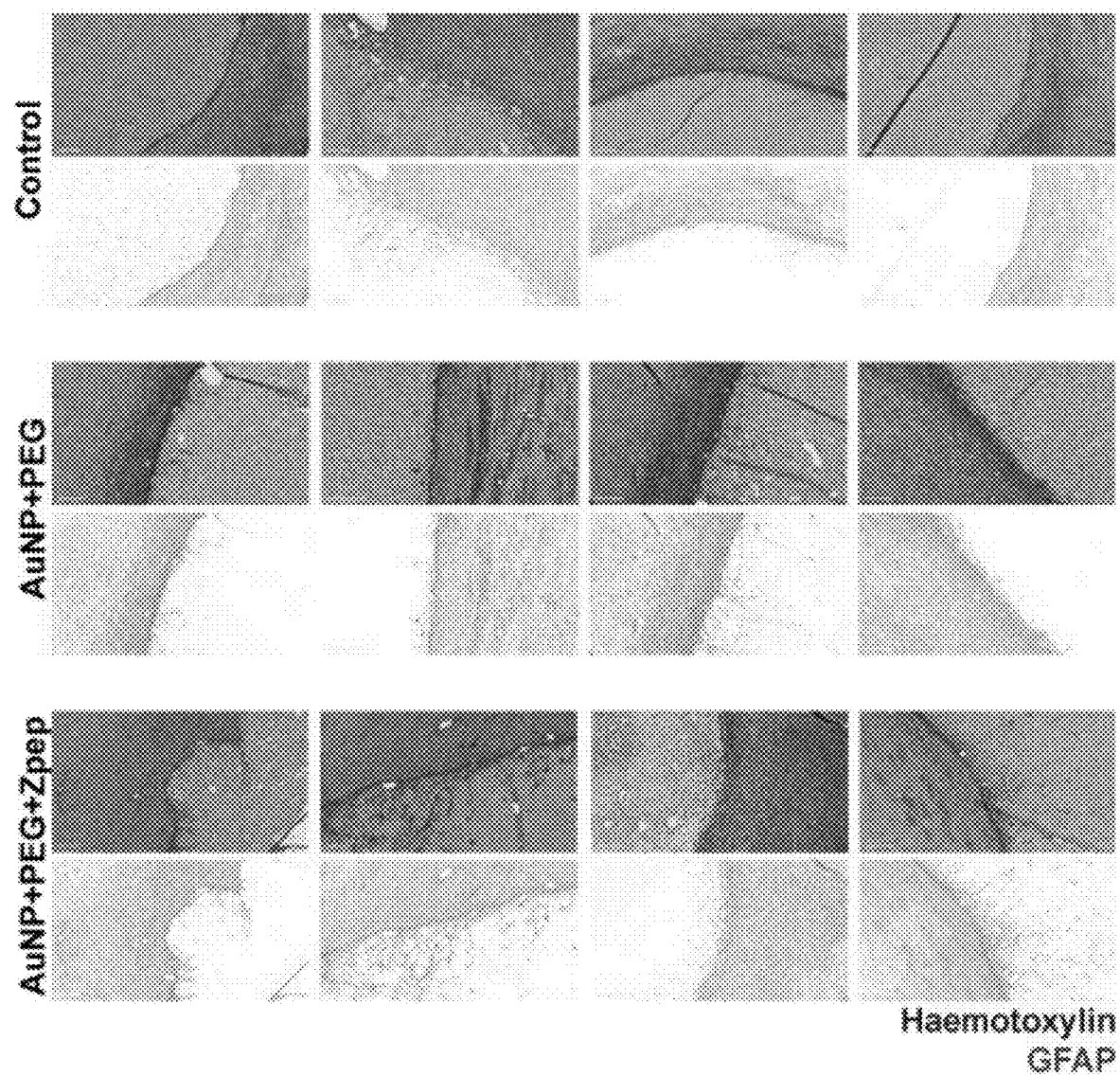
FIG. 9 depicts astrocyte activation in AuNP, AuNP-PEG, and AuNP—Z-treated animals.

Astrocyte activation in gold nanoparticle and AuNP—Z-treated animals (FIG. 9). FIG. 9 depicts astrocyte activation in AuNP, AuNP—PEG, and AuNP—Z-treated animals. In particular, FIG. 9 shows astrocyte activation at the border between normal brain tissue and the tumor mass. Individual color micrographs represent a unique animal. The pseudo-colored brown channel image below each color micrograph shows astrocyte activation as assessed by GFAP reactivity. While activated astrocytes are present in all groups, AuNP—Z treated animals show activation of astrocytes both within and outside the tumor mass, with denser GFAP staining in comparison to other groups. (Scale bar is 200 μm)

What is claimed is:

1. A composition comprising a conjugate, the conjugate comprising: (1) a gold nanoparticle; (2) optionally, a linker or a masking agent; and (3) a ligand,
    wherein the ligand comprises an isolated water-soluble mixture of zymosan polypeptides obtained by extracting zymosan with an extraction buffer comprising CHAPS detergent and applying the CHAPS detergent extract to a 10 kDa centrifugal spin column, and
    wherein the conjugate has a diameter of about 50 nm to about 200 nm.

2. The composition of claim 1, wherein the linker or masking agent comprises PEG, a PEG derivative, or a hydrophilic polycarbonate.

3. The composition of claim 1, wherein the ligand further comprises one or more of peptidoglycan, LPS, zymosan, Pam3CSK4, amyloid-beta peptide, lipoteichoic acid, HMGB1, heat shock proteins, CSF-1R inhibitors, LPS+IFN-gamma, xyloside, IFN-gamma, TNF-alpha, IL-2, lipocalin 2, miRNA-155, or a combination thereof.

4. A composition comprising: (1) a nanoparticle; and (2) a ligand, wherein the ligand comprises an isolated water-soluble mixture of zymosan polypeptides obtained by extracting zymosan with an extraction buffer comprising CHAPS detergent and applying the CHAPS detergent extract to a 10 kDa centrifugal spin column, wherein the nanoparticle forms a conjugate with the ligand or encapsulates the ligand, and wherein the conjugate or the nanoparticle encapsulating the ligand has a diameter of about 5 nm to about 200 nm and is capable of crossing the blood brain barrier.

5. The composition of claim 4, further comprising PEG, a PEG derivative, a hydrophilic polycarbonate, or a derivative thereof.

6. The composition of claim 4, wherein the nanoparticle comprises a gold nanoparticle.

7. The composition of claim 4, wherein the conjugate or the nanoparticle encapsulating the ligand has a diameter of about 50 nm to about 200 nm.

8. The composition of claim 4, wherein the ligand further comprises one or more of peptidoglycan, LPS, zymosan, Pam3CSK4, amyloid-beta peptide, lipoteichoic acid, HMGB1, heat shock proteins, CSF-1R inhibitors, LPS+IFN-gamma, xyloside, IFN-gamma, TNF-alpha, IL-2, lipocalin 2 miRNA-155, or a combination thereof.

9. The composition of claim 1 wherein the isolated water-soluble mixture of zymosan polypeptides is formed by a process comprising:
    snap freezing the zymosan;
    crushing the snap frozen zymosan;
    mixing the crushed zymosan and the extraction buffer comprising the CHAPS detergent to obtain the CHAPS detergent extract;
    centrifuging the CHAPS detergent extract and collecting the supernatant; and
    applying the supernatant to the 10 kDa centrifugal spin column to concentrate the isolated water-soluble mixture of zymosan polypeptides.

10. The composition of claim 4 wherein the isolated water-soluble mixture of zymosan polypeptides is formed by a process comprising:
    snap freezing the zymosan;
    crushing the snap frozen zymosan;
    mixing the crushed zymosan and the extraction buffer comprising the CHAPS detergent to obtain the CHAPS detergent extract;
    centrifuging the CHAPS detergent extract and collecting the supernatant; and
    applying the supernatant to the 10 kDa centrifugal spin column to concentrate the isolated water-soluble mixture of zymosan polypeptides.

* * * * *